US00RE40535E

(19) United States
(12) Reissued Patent
Couto et al.

(10) Patent Number: US RE40,535 E
(45) Date of Reissued Patent: Oct. 7, 2008

(54) ANTI-KC4 HUMANIZED MONOCLONAL ANTIBODY AND CELLS THAT EXPRESS THE ANTIBODY

(75) Inventors: Fernando J. R. do Couto, Pleasanton, CA (US); Roberto L. Ceriani, Lafayette, CA (US); Jerry A. Peterson, Eureka, CA (US)

(73) Assignee: IBC Pharmaceuticals, Inc., Morris Plains, NJ (US)

(21) Appl. No.: 10/144,047

(22) Filed: May 14, 2002

(Under 37 CFR 1.47)

Related U.S. Patent Documents

Reissue of:
(64) Patent No.: 6,281,335
Issued: Aug. 28, 2001
Appl. No.: 08/134,346
Filed: Oct. 8, 1993

(51) Int. Cl.

| | |
|---|---|
| ***C07K 16/00*** | (2006.01) |
| ***A61K 49/00*** | (2006.01) |
| ***C12N 5/16*** | (2006.01) |
| ***G01N 33/53*** | (2006.01) |

(52) U.S. Cl. ..... 530/388.85; 530/388.8; 530/387.1; 530/387.3; 424/9.1; 424/133.1; 424/130.1; 424/156.1; 436/518; 435/7.95; 435/328

(58) Field of Classification Search ..... 424/9.1, 424/130.1, 133.1, 156.1; 530/388.85, 388.8, 530/387.1, 387.3; 435/7.95, 328, 7
See application file for complete search history.

(56) References Cited

U.S. PATENT DOCUMENTS

| | | | |
|---|---|---|---|
| 4,708,930 | A | 11/1987 | Kortright |
| 5,075,219 | A | 12/1991 | Ceriani et al. |
| 5,077,220 | A | 12/1991 | Ceriani et al. |

FOREIGN PATENT DOCUMENTS

| | | |
|---|---|---|
| GB | 2 188 638 | 10/1988 |

OTHER PUBLICATIONS

Cruse et al., Illustrated Dictionary of Immunology, CRC Press, p. 144, 1994.*
Freshney (Culture of Animal Cells, A Manual of Basic Technique, Alan R. Liss, Inc., 1983, New York, p. 4*
Dermer (Bio/Technology, 1994, 12:320.*
Seaver (1994; Genetic Engineering vol. 14(14): pp. 10 and 21.*
Gura (Science, 1997, 278:1041–1042.*
Jain (Sci. Am., 1994, 271:58–65.*
Trickett (Medical Laboratory sciences 47:120–131, 1990.*
Treleaven et al (Hematological Oncology 3:36–75, 1985.*
Morrison et al., *Proc. Natl. Acad. Sci*, 81:6851–6855, Nov. 1984.
E.A. Padlan, *Molecular Immunology*, 28:4/5:489–498, 1991.
J.A. Peterson et al., *Biochemical and Histological Characterization of Antigens Preferentially Expressed on the Surface and Cytoplasm of Breast Carcinoma Cells Identified by Monoclonal Antibodies Against the Human Milk Fat Globule, Hybridoma* 9:221–235, 1990.
D. R. Davies and E. A. Padlan, *Antibody–Antigen Complexis, Annu. Rev. Biochem*, 59:439–73, 1990.
L. Reichmann et al., *Reshaping Human Antibodies for Therapy, Nature*, 332:323–327, 1988.
Dienhart, D.G., et al., "Imaging of non–small cell lung cancers with a monoclonal antibody, KC–4G3, which recognizes a human milk fat globule antigen," Cancer Res. 50(21):7068–76 (Nov. 1, 1990) (plus Abstract).
Longley, C., et al., "Pharmacokinetics, biodistribution, and gamma camera imaging of $^{111}$In–KC–4G3 murine monoclonal antibody in athymic nude mice with or without human tumor xenografts," *Cancer Res.* 50(18):5954–61 (Sep. 15, 1990).

* cited by examiner

*Primary Examiner*—Sheela J. Huff
(74) *Attorney, Agent, or Firm*—Foley & Lardner LLP

(57) ABSTRACT

An anti-KC-4 humanized monoclonal antibody that comprises the variable regions of the light and heavy chains of the anti-KC-4 murine antibody, wherein the light chain has 7 amino acids and the heavy chain has 12 amino acids of the framework regions substituted with amino acid present in equivalent positions in antibodies of a species other than munne, and the constant regions of a human antibody. The antibody may be labeled and/or glycosylated, and is presented as a composition with a carrier. The anti-KC-4 monoclonal antibody is used in diagnostic kits for cancer and in in vivo methods of imaging and treating a primary or metastasized cancer, and in vitro diagnosis and ex vivo purging neoplastic cells from a biological fluid. RNAs and DNAs encode the monoclonal antibody, and a hybrid vector carrying the nucleotides and transfected cells express the peptides.

19 Claims, No Drawings

ANTI-KC4 HUMANIZED MONOCLONAL ANTIBODY AND CELLS THAT EXPRESS THE ANTIBODY

Matter enclosed in heavy brackets [ ] appears in the original patent but forms no part of this reissue specification; matter printed in italics indicates the additions made by reissue.

BACKGROUND OF THE INVENTION

1. Field of the Invention

The invention relates to the in vito and in vivo diagnosis and therapy of carcinomas by means of a specifically targeted humanized mouse monoclonal antibody selectively binding the human KC-4 antigen. The humanized anti-KC-4 mouse antibody comprises the complementarity determining regions (CDRs) of the variable regions of the mouse antibody of the same specificity, and its framework regions having specific amino acids replaced in a predetermined manner, and the constant regions of a human antibody. The humanized anti-KC-4 mouse antibody of this invention is expected to elicit a lesser immunological response in humans than the whole mouse antibody and is therefore considered suitable for in vivo administration to humans. Polynucleotide segments encoding the humanized antibody, a hybrid vector and a transfected host cell carrying the DNA segments encoding the antibody are useful for preparing the peptides disclosed herein.

2. Description of the Background

Carcinomas result from the carcinogenic transformation of cells of different epithelia. Two of the most damaging characteristics of carcinomas are their uncontrolled growth and their ability to create metastases in distant sites of the host, particularly a human host. It is usually these distant metastases that cause serious consequences to the host, since frequently the primary carcinoma may be, in most cases, removed by surgery. The treatment of metastatic carcinomas, that are seldom removable, depends on irradiation therapy and systemic therapies of different natures. The systemic therapies currently include, but not fully comprise, chemotherapy, radiation, hormone therapy, different immunity-boosting medicines and procedures, hyperthermia and systemic monoclonal antibody treatment. The latter can be labeled with radioactive elements, immunotoxins and chemotherapeutic drugs.

Radioactively labeled monoclonal antibodies were initially used with success in lymphomas and leukemia, and recently in some carcinomas. The concept underlying the use of labeled antibodies is that the labeled antibody will specifically seek and bind to the carcinoma and, the radioactive element, through its decay, will irradiate the tumor in situ. Since radioactive rays travel some distance in tumors it is not necessary that every carcinoma cell bind the labeled antibody. The specificity of the monoclonal antibodies will permit a selective treatment of the tumor while avoiding the irradiation of innocent by-stander normal tissues, that could be dose limiting. Chemotherapy produces serious toxic effects on normal tissues, making the chemotherapy of carcinomas less than desirable, and the use of radiolabeled monoclonal antibodies a valid alterative.

Non-human antibodies raised against human epitopes have been used for the diagnosis and therapy of carcinomas as is known in the art. Also known are the methods for preparing both polyclonal and monoclonal antibodies. Examples of the latter are BrE-2, BrE-3 and KC-4 (e.g. U.S. Pat. Nos. 5,077,220; 5,075,219 and 4,708,930.

The KC-4 murine monoclonal antibody is specific to a unique antigenic determinant, the "antigen", and selectivity binds strongly to neoplastic carcinoma cells and not to normal human tissue (U.S. Pat. No. 4,708,930 to Coulter). The antigen appears in two forms in carcinoma cells, only the smaller of these forms being expressed in the cell membrane. The larger form appears only in the cytoplasm and has an approximate 490 Kdalton molecular weight (range of 480,000–510,000). The second form occurs at a higher density of expression, is found both in the cytoplasm and the membrane of carcinoma cells and has an approximate 438 Kdalton molecular weight (range of 390,000–450,000) as determined by gel electrophoresis with marker proteins of known molecular weights. Labeled KC-4 was applied to the diagnosis and medical treatment of various carcinomas, particularly adenocarcinoma and squamous cell carcinoma regardless of the human organ site of origin.

The BrE-3 antibody (Peterson et al., Hybridoma 9:221 (1990); U.S. Pat. No 5,075,219) was shown to bind to the tandem repeat of the polypeptide core of human breast epithelial mucin. When the mucin is deglycosylated, the presence of more tandem repeat epitopes is exposed and the binding of the antibody increases. Thus, antibodies such as BrE-3 bind preferentially to neoplastic carcinoma tumors because these express an unglycosylated form of the breast epithelial mucin that is not expressed in normal epithelial tissue. The preferential binding combined with an observed low concentration of epitope for these antibodies in the circulation of carcinoma patients, such as breast cancer patients, makes antibodies having specificity for a mucin epitope highly effective for carcinoma radioimmunotherapy. A $^{90}$Y-BrE-3 radioimmunoconjugate proved highly effective against human breast carcinomas transplated into nude mice. Human clinical studies showed the $^{90}$Y-BrE-3 radioimmunoconjugate to considerably reduce the size of breast tumor metastases without any immediate toxic side effects. Moreover, an $^{111}$In-BrE-3 radioimmunoconjugate was successfully used for imaging 15 breast cancer patients, providing excellent tumor targeting in 13 out of 15 of the patients. Out of all the breast tumor metastases occurring in another study, 86% were detected by $^{111}$In-BrE-3. Unfortunately, 2 to 3 weeks after treatment, the patients developed a strong human anti-murine antibody (HAMA) response that prevented further administration of the radioimmunoconjugate. The HAMA response, which is observed for numerous murine monoclonal antibodies, precludes any long-term administration of murine antibodies to human patients. Similarly, other heterologous antibodies, when administered to humans, elicited similar antibody responses. The anti-heterologous human response is, thus, a substantial limiting factor hindering the successful use of heterologous monoclonal antibodies as therapeutic agents, which could, otherwise, specifically annihilate breast carcinomas, causing little or no damage to normal tissue and having no other toxic effects.

Chimeric antibodies are direct fusions between variable domains of one species and constant domains of another. Murine/human chimeric antibodies prepared from other types of B cells binding to other types of antigenic determinants have been shown to be less immunogenic in humans than wide murine antibodies. These proved to be less immunogenic but still in some cases an immune response is mounted to the rodent variable region framework region (FR). A further reduction of the "foreign" nature of the chimeric antibodies was achieved by grafting only the CDRs from a rodent monoclonial into a human supporting framework prior to its subsequent fusion with an appropriate constant domain (European Patent Application, Publication No. 239,400 to Winter; Riechmann, et al., Nature 332:323–327 (1988)). However, the procedures employed to accomplish CDR-grafting often result in imperfectly "humanized" antibodies. That is to say, the resultant antibody loses affinity (usually 2–3 fold, at best).

The ligand binding characteristics of an antibody combining site are determined primarily by the structure and relative disposition of the CDRs, although some neighboring residues also have been found to be involved in antigen binding (Davies, et al., Ann Rev. Biochem. 59:439–473 (1990)).

The technologies of molecular biology have further expanded the utility of many antibodies by allowing for the creation of class switched molecules whose functionality has been improved by the acquisition or loss of complement fixation. The size of the bioactive molecule may also be reduced so as to increase the tissue target availability of the antibody by either changing the class from the IgM to an IgG, or by removing most of the heavy and light chain constant regions to form an $F_V$ antibody. Common to all of these potentially therapeutic forms of antibody are the required complementary determining regions (CDRs), which guide the molecule to its ligand, and the framework residues (FRs) which support the CDRs and dictate their disposition relative to one another. The crystallographic analysis of numerous antibody structures revealed that the antigen combining site is composed almost entirely of the CDR residues arranged in a limited number of loop motifs. The necessity of the CDRs to form these structures, combined with the appreciated hypervariability of their primary sequence, leads to a great diversity in the antigen combining site, but one which has a finite number of possibilities. Thus, its hypermutability and the limited primary sequence repertoire for each CDR would suggest that the CDRs derived for a given antigen from one species of animal would be the same derived from another species. Hence, they should be poorly immunogenic, if at all, when presented to a recipient organism.

Accordingly, there is still a need for a product of high affinity and/or specificity for carcinoma antigens suitable for the detection and therapy of carcinomas which elicits a lesser antibody response than whole non-human antibodies or chimeric antibodies containing, for instance the entire non-human variable region.

SUMMARY OF THE INVENTION

This invention relates to a humanized mouse monoclonal antibody and its glycosylated derivative which specifically and selectively bind to the human KC-4 antigen, the antibody consisting essentially of the variable regions of the light and heavy chains of the anti-KC-4 mouse antibody having the ATCC No. HB 8710 or HB 8709, wherein specific amino acids in the FR are substituted per chain with amino adds present in equivalent positions in antibodies of other species, and the constant region of a human antibody.

Also provided are the corresponding DNA and RNA segments encoding the monoclonal antibody, a hybrid vector carrying the DNA, and a transfected host thereof.

Still part of this invention are in vitro methods of diagnosing cancer and for conducting immunohistochemistry assays of tissue slices, an ex vivo method of purging neoplastic cells, and in vivo methods for imaging and therapy of cancer patients.

Other objects, advantages and features of the present invention will become apparent to those skilled in the art from the following discussion.

DESCRIPTION OF THE PREFERRED EMBODIMENTS

This invention arose from a desire by the inventors to improve on antibody technology suitable for use in diagnostic and therapeutic applications, particularly for in vivo administration. The useful monoclonal antibodies obtained up to the present time have been prepared by fusing immortalized cell lines with B-cells of mouse or other animal origin. However, in general, heterologous antibodies may only be administered once to a human due to the detrimental immunological effects they elicit. This is true for most heterologous antibodies administered For example, the repeated administration of murine antibodies to a subject elicits a strong human anti-murine antibody (HAMA) response, which precludes their further utilization as therapeutic agents in humans. These heterologous antibodies initiate an immediate adverse reaction in many human patients and are, thus, rendered inaffective for further administration as therapeutic agents. On the other hand, human monoclonal hybridoma cell lines have not yet been very stable and have, therefore, not been suitable for the large scale, repeated production of monoclonal antibodies.

The present inventors, thus, have undertaken the preparation of anti-KC-4 humanized monoclonal antibodies maintaining the entire CDRs of the mouse antibodies of the same specificity and human constant regions, and substituting 7 amino acids in the heavy chain and 12 amino acids in the light chain, the substituted amino acids being positioned in the framework regions (FRs) and being selected from those present in equivalent positions in other human antibodies, and the constant regions of a human antibody. The [hybridomas] *cells* of the invention can produce large quantities of monoclonal antibodies having a desirable high affinity, specificity and selectivity for the human KC-4 antigen.

The present inventors have found, surprisingly, that these monoclonal antibodies substantially preserve the binding, specificity and selectivity of the whole corresponding mouse antibody while they are expected to elicit a less [detnmental] *detrimental* immunological response. However, the simple preservation of the binding region of an antibody does not by itself ensure that the binding characteristics of the antibody will be maintained. Antibodies are glycopolypeptides that are folded into specific conformations. When the glycoside portion of the molecule or portions of the amino acid sequence are perturbed or excised, the folding pattern of the molecule may be perturbed. Thus, any deletion or modification of the sequence of an antibody must be made taking into consideration that its folding dependent properties may be diminished or even obliterated if the folding is substantially affected, even though the amino acid sequences involved in the binding of the antigen are preserved.

The present inventors selected the following strategy for the preparation and manufacture of the antibodies of this invention. The cDNAs that encode the variable chains of an antibody may be obtained by isolation of mRNAs from hybridoma cells and their mRNAs reversely transcribed. The thus obtained cDNAs may be amplified by the polymerase chain reaction (PCR) and the DNAs obtained inserted into a vector, and optionally sequenced and restriction enzyme cut. Thus, the cDNAs encoding the variable chain (F.sub.V) region of the light (V.sub.L) and heavy (V.sub.H) chains of an antibody having affinity and specificity for the human KC-4 antigen may be reverse transcribed from the isolated mRNAs. The variable region cDNAs may then be modified, with predesigned primers used to PCR amplify them or synthesized de novo, cloned into a vector optionally carrying DNA sequences encoding the human contrast region(s), optionally sequenced, and then transfected into host cells for expression of the humanized [anti-LC-4] *anti-KC-4* antibodies. The binding specifications and binding constants of the humanized antibodies may then be determined and compared to those of the whole mouse antibodies.

X-ray crystallographic studies demonstrate that the framework structures of the F.sub.V of different antibodies assume a canonical structure regardless of the species of origin, amino acid sequence, or ligand specificity. This is generally taken as evidence that the ligand-binding characteristics of an antibody combining site are determined primarily by the structure and relative disposition of the CDRs, although some neighboring framework residues may also be involved in antigen-binding. Thus, if the fine specificity of an antibody is to be preserved, its [CRD] *CDR* structures, and parts of the neighboring residues, their interaction with each other and with the rest of the valuable domains, must also be maintained. These crystallographic studies point to the possible need for retaining most, if not all, of the many interior and inter-domain contact residues since the structural effects of replacing only a few of them cannot be predicted.

While at first the necessity of keeping these amino acids might seem to defeat the goal of decreasing immunogencity by "humanization", the actual number of amino acids that must be retained has been determined by the inventors to be small because of the striking similarity between human and murine variable regions. Moreover, many if not most, of the retained amino acids posses side chains that are not exposed on the surface of the molecules and, therefore, may not contribute to its antigenicity. Clearly, it is most of the exposed amino acids that are good candidates for substitution since it is these amino acids that are exposed to the immunological environment of a mammal and may form epitopes of increased immunogenicity.

The challenge in humanizing the variable regions of the anti-KC-4 mouse antibody thus begins with the identification of the "important" heterologous amino acids. "Important" amino acids are defined herein as those, for example, that are involved in antigen binding, contact the CDRs and the opposite chains, and have buried side chains. Ideally, these residues might be identified from a well characterized three-dimensional structure. However, when, as in the present case, direct structural data are not available, the inventors have, fortunately, made it possible to predict the location of these important amino acids by analyzing other related antibody structures, especially those whose variable light and heavy regions belong to the same class. The classes of variable regions can be determined from their amino acid sequence.

One method by which these important amino acids may be identified has been described for the case of the amino acids with buried side chains by Padlan, E. A. (Padlan, E. A., "A Possible Procedure for Reducing the Immunogenicity of Antibody Variable Domains While Preserving Their Ligand-Binding Properties", Molecular Immunology, 28:489–494 (1991)). In the present case, various antibody variable region structures were compared using a computerized program that determines the solvent accessibility of the framework residues as well as their contacts with the opposite domain as described by Padlan, E. A. (1991), supra. Surprisingly, a close examination of the fractional solvent accessibility reveals a very close similarity in the exposure patterns of the $V_H$ and the $V_L$ domains. Put in simple terms, regardless of the particular antibody in question, and of its amino acid sequence, the inventors have found that the buried residues occupy similar relative positions in most antibodies.

A similar analysis can be done by computer modeling, to determine which amino acids contact the CDRs and which contact the opposite domain. At this point, the Fab structures that are currently in the Protein Data bank (Bernstein, F. C., et al., J. Mol. Biol. 112:535–542 (1977)) may be examined to determine which FRs may be important in maintaining the structure of the combining site. Thus, after a close inspection of many high resolution three-dimensional structures of variable regions, the positions of all important framework amino acids, that is, those that contact the CDRs, the opposite domain, and those whose side chains are inwardly pointed, may be tabulated. Keeping these amino acids, as well as those from the CDRs, and finally those FR amino acids that may be involved in ligand binding, should insure to a great extent the preservation of affinity. The precise identification of FR amino acids that are involved in ligand-binding cannot be generalized since it varies for different antibodies. Nevertheless, conservative decisions can be made to preserve the amino acids located in FRs that have a high probability of contacting the antigen. These regions are generally located immediately adjacent to the CDRs and at the N-terminus of both chains, because the surfaces of these regions are contiguous with the CDR surfaces.

Surprisingly, it is possible to keep all of these important amino acids in a heterologous humanized antibody and still increase dramatically the similarity with a human consensus sequence. That is, the final number of amino acids with murine identities differing from human identities that are kept is typically small. This is possible because human frameworks that are similar to the murine frameworks, especially at the positions of the important amino acids, can be found. This is because many of the important amino acids have the same identities in both murine and human antibodies.

All the amino acids that are determined to be not important by the method described above may be replaced by their corresponding human counterparts. The surface of the finally humanized antibody should look very much like that of a human antibody except for the antigen binding surfaces. The original shape of those binding surfaces, however, is maintained by leaving the internal composition of the antibody intact, preserving inter-domain contacts and by keeping very few key amino acids that contact the CDRs.

a) Choosing the Best Human Framework to Use in the "Humanization" of an Antibody When its Structure is Known At the present time, there are 11 Fab structures for which the atomic coordinates are known and have been placed in the Protein Data Bank as shown in Table 1 below, 2 from human and 9 from murine antibodies.

TABLE 1

Fab Structures for Which Coordinates are in the Protein Data Bank

| | ANTIBODY | RESOLUTION (A) | R-VALUE | PDB CODE |
|---|---|---|---|---|
| HUMAN | NEWM | 2.0 | 0.46 | 3FAB |
| | KOL | 1.9 | 0.189 | 2FB4 |
| MURINE | McPC603 | 2.7 | 0.225 | 1MCP |
| | J539 | 1.95 | 0.194 | 2FBJ |
| | HyHEL-5 | 2.54 | 0.245 | 2HFL |
| | HyHEL-10 | 3.0 | 0.24 | 3HFM |
| | R19.9 | 2.8 | 0.30 | 1F19 |
| | 4-4-20 | 2.7 | 0.215 | 4FAB |
| | 36-71 | 1.85 | 0.248 | 6FAB |
| | B13I2 | 2.8 | 0.197 | 1IGF |
| | D1.3 | 2.5 | 0.184 | 1FDL |

The contacts between side chains in the variable domains of the 11 Fabs have been collected and are presented in Tables 2 to 4 below. The framework (FR) amino acids in the $V_L$ domains that contact CDRs are listed in Table 2 below.

TABLE 2

$V_L$ Framework Residues That Contact CDR Residues in Fabs of Known Three-Dimensional Structure

| | ANTIBODY | | | | | | | | | | |
|---|---|---|---|---|---|---|---|---|---|---|---|
| POSITION | J539 | McPC603 | HyHEL-10 | HyHEL-5 | R19.9 | 4-4-20 | 36-71 | B13I2 | D1.3 | NEWM | KOL |
| 1 | GLU(2) | ASP(5) | ASP(10) | ASP(3) | | ASP(8) | ASP(4) | | ASP(11) | | |
| 2 | ILE(11) | ILE(15) | ILE(17) | ILE(13) | ILE(5) | VAL(9) | ILE(20) | VAL(9) | ILE(10) | SER(3) | |
| 3 | | VAL(3) | VAL(2) | VAL(3) | GLN(2) | VAL(2) | GLN(2) | LEU(6) | | VAL(2) | |
| 4 | LEU(7) | MET(6) | LEU(6) | LEU(10) | MET(9) | MET(13) | MET(7) | MET(6) | MET(7) | LEU(4) | LEU(6) |
| 5 | | THR(1) | | | THR(1) | THR(2) | | | | THR(1) | |
| 7 | | | | | | | | THR(4) | | | |
| 22 | | | | | | | | SER(6) | | | |
| 23 | CYS(1) | CYS(1) | CYS(2) | CYS(2) | CYS(1) | CYS(1) | CYS(1) | | | | CYS(1) |
| 35 | TRP(3) | TRP(2) | TRP(4) | | TRP(2) | | TRP(5) | TRP(4) | TRP(4) | TRP(1) | TRP(2) |
| 36 | TYR(12) | TYR(16) | TYR(8) | TYR(10) | TYR(22) | TYR(13) | TYR(15) | TYR(8) | TYR(14) | TYR(13) | TYR(11) |
| 45 | | | | | LYS(12) | LYS(5) | | | | | |
| 46 | PRO(3) | LEU(6) | LEU(4) | ARG(15) | LEU(5) | VAL(14) | LEU(5) | LEU(10) | LEU(6) | LEU(2) | LEU(6) |
| 48 | ILE(1) | ILE(1) | ILE(1) | | | | ILE(3) | ILE(2) | VAL(1) | | ILE(1) |
| 49 | TYR(28) | TYR(29) | LYS(13) | TYR(12) | TYR(40) | TYR(22) | TYR(22) | TYR(16) | TYR(25) | | TYR(25) |
| 58 | VAL(3) | VAL(3) | ILE(1) | VAL(6) | VAL(6) | VAL(5) | VAL(4) | VAL(5) | VAL(1) | | VAL(6) |
| 60 | | ASP(1) | | | | ASP(2) | | ASP(4) | | | ASP(2) |
| 62 | | | | PHE(1) | | PHE(1) | PHE(1) | | | | |
| 66 | | | | | | | | | | LYS(2) | LYS(11) |
| 67 | | SER(3) | | | | | | | SER(1) | | |
| 69 | | THR(3) | THR(3) | | | THR(5) | THR(1) | THR(4) | THR(1) | SER(1) | |
| 70 | | ASP(2) | | | ASP(1) | | ASP(6) | | | SER(2) | |
| 71 | TYR(14) | PHE(23) | PHE(17) | TYR(17) | TYR(24) | PHE(1) | TYR(17) | PHE(19) | TYR(16) | ALA(3) | ALA(4) |
| 88 | CYS(1) | | CYS(2) | | CYS(1) | CYS(1) | CYS(1) | CYS(1) | CYS(2) | | CYS(1) |
| 98 | PHE(8) | PHE(8) | PHE(10) | PHE(5) | PHE(8) | PHE(4) | PHE(8) | PHE(14) | PHE(14) | PHE(3) | PHE(7) |

Those FR in the $V_H$ domains that contact CDRs are listed in Table 3 below.

TABLE 3

$V_H$ Framework Residues That Contact CDR Residues in Fabs of Known Three-Dimensional Structure

| | ANTIBODY | | | | | | | | | | |
|---|---|---|---|---|---|---|---|---|---|---|---|
| POSITION | J539 | McPC603 | HyHEL-10 | HyHEL-5 | R19.9 | 4-4-20 | 36-71 | 913I2 | D1.3 | NEWM | KOL |
| 1 | | | | | | | GLU(3) | | | | |
| 2 | VAL(11) | VAL(3) | VAL(8) | | VAL(1) | | VAL(7) | VAL(3) | VAL(12) | | VAL(9) |
| 4 | LEU(2) | LEU(5) | LEU(5) | | LEU(2) | LEU(1) | LEU(1) | LEU(1) | LEU(1) | | LEU(1) |
| 24 | | THR(2) | VAL(6) | | | ALA(1) | | | | | |
| 27 | PHE(3) | PHE(2) | | TYR(14) | TYR(11) | PHE(26) | TYR(4) | PHE(4) | PHE(4) | THR(1) | PHE(3) |
| 28 | ASP(3) | THR(5) | | THR(3) | THR(6) | THR(4) | THR(2) | THR(3) | | SER(1) | ILE(2) |
| 29 | PHE(4) | PHE(4) | | PHE(10) | PHE(7) | PHE(13) | PHE(6) | PHE(3) | LEU(1) | | PHE(4) |
| 30 | | | THR(2) | | THR(6) | SER(7) | | | | ASP(5) | |
| 36 | | | | | | | TRP(2) | | | | |
| 37 | | VAL(1) | | | VAL(1) | | | | VAL(1) | VAL(2) | VAL(1) |
| 38 | ARG(1) | ARG(2) | ARG(4) | LYS(2) | LYS(1) | ARG(4) | LYS(2) | ARG(1) | | | ARG(3) |
| 40 | | | | ARG(1) | | | | | | | |
| 46 | GLU(3) | GLU(4) | GLU(1) | GLU(2) | GLU(3) | GLU(4) | GLU(9) | | GLU(1) | | GLU(1) |
| 47 | TRP(21) | TRP(29) | TYR(20) | TRP(21) | TRP(13) | TRP(18) | TRP(21) | TRP(23) | TRP(19) | TRP(22) | TRP(15) |
| 48 | ILE(1) | ILE(1) | MET(6) | ILE(12) | ILE(13) | VAL(1) | ILE(9) | VAL(3) | LEU(1) | ILE(2) | VAL(1) |
| 49 | | ALA(2) | | | | ALA(2) | | ALA(2) | | | ALA(2) |
| 66 | | | ARG(11) | | | ARG(3) | | ARG(2) | | ARG(2) | ARG(1) |
| 67 | PHE(4) | PHE(10) | ILE(9) | ALA(1) | | PHE(11) | THR(5) | PHE(12) | LEU(6) | VAL(2) | PHE(10) |
| 68 | | ILE(1) | | | THR(1) | THR(11) | | | | | THR(2) |
| 69 | ILE(8) | VAL(6) | ILE(8) | PHE(12) | LEU(5) | ILE(20) | LEU(6) | ILE(11) | ILE(8) | MET(4) | ILE(9) |
| 71 | ARG(7) | ARG(16) | ARG(2) | ALA(1) | VAL(4) | ARG(6) | VAL(6) | ARG(3) | LYS(4) | | ARG(9) |
| 73 | ASN(1) | THR(3) | | | | ASP(3) | | | | | |
| 76 | LEU(4) | LEU(7) | TYR(9) | ALA(1) | ALA(1) | VAL(2) | ALA(1) | LEU(6) | VAL(4) | PHE(5) | LEU(5) |
| 80 | | | | | | LEU(1) | | | | | |
| 82 | | | LEU(2) | | | | | | MET(1) | LEU(1) | |
| 86 | | | | | | ASP(2) | | | | | |
| 92 | | | | CYS(1) | | | CYS(1) | | CYS(1) | | |
| 93 | ALA(4) | ALA(5) | | LEU(2) | | THR(3) | ALA(1) | THR(5) | ALA(4) | ALA(1) | ALA(3) |
| 94 | ARG(38) | ARG(24) | ASN(11) | HIS(2) | ARG(30) | | ARG(23) | ARG(14) | ARG(30) | ARG(22) | ARG(27) |
| 103 | TRP(5) | TRP(9) | | | TRP(2) | TRP(2) | TRP(5) | | TRP(2) | TRP(4) | TRP(4) |

The FR amino acids, that contact the opposite domain and which presumably are the ones mainly responsible for the quaternary structure of the $F_V$ domains are listed in Table 4 below.

TABLE 4

Framework Residues That Contact Framework Residues in the Opposite Domain in Fabs of Known Three-Dimensional Structure

| | ANTIBODY | | | | | | | | | | |
|---|---|---|---|---|---|---|---|---|---|---|---|
| POSITION | J539 | McPC603 | HyHEL-10 | HyHEL-5 | R19.9 | 4-4-20 | 36-71 | 913I2 | D1.3 | NEWM | KOL |
| IN $V_L$: | | | | | | | | | | | |
| 36 | TYR(3) | TYR(4) | TYR(3) | TYR(5) | | TYR(11) | TYR(7) | TYR(1) | TYR(7) | | TYR(5) |
| 38 | GLY(10) | GLN(4) | GLN(9) | GLN(5) | GLN(5) | GLN(3) | GLN(6) | GLN(12) | GLN(6) | GLN(7) | GLN(8) |
| 43 | SER(7) | PRO(1) | SER(8) | SER(5) | THR(3) | | | SER(3) | SER(2) | ALA(5) | ALA(1) |
| 44 | PRO(10) | PRO(14) | PRO(8) | PRO(11) | | PRO(7) | ILE(20) | PRO(16) | PRO(16) | PRO(7) | PRO(13) |
| 46 | PRO(3) | | | | | | | | | | |
| 85 | | | MET(2) | | THR(5) | | | VAL(1) | | ASP(12) | |
| 87 | TYR(6) | TYR(4) | PHE(6) | TYR(2) | | | PHE(5) | TYR(10) | TYR(8) | TYR(6) | TYR(6) |
| 98 | PHE(11) | PHE(8) | PHE(7) | PHE(12) | PHE(12) | PHE(12) | PHE(8) | PHE(13) | PHE(12) | PHE(10) | PHE(15) |
| 100 | | ALA(2) | | | | | | | | | |
| IN $V_B$: | | | | | | | | | | | |
| 37 | VAL(4) | | ILE(2) | VAL(1) | VAL(4) | VAL(2) | VAL(1) | VAL(2) | VAL(4) | VAL(1) | VAL(4) |
| 39 | GLN(10) | GLN(4) | LYS(8) | GLN(5) | GLN(5) | GLN(3) | GLN(6) | GLN(10) | GLN(6) | GLN(4) | GLN(7) |
| 43 | | | ASN(4) | | GLN(7) | | | LYS(6) | | ARG(19) | |
| 44 | | ARG(2) | | | | | | | | | |
| 45 | LEU(13) | LEU(12) | LEU(6) | LEU(14) | | LEU(8) | LEU(11) | LEU(13) | LEU(14) | LEU(11) | LEU(16) |
| 47 | TRP(1) | | TYR(2) | | TRP(2) | | | | TRP(3) | TRP(2) | |
| 91 | TYR(6) | TYR(4) | TYR(3) | TYR(8) | PHE(3) | TYR(2) | PHE(4) | TYR(3) | TYR(5) | TYR(3) | |
| 103 | TRP(11) | TRP(15) | TRP(16) | TRP(11) | TRP(4) | TRP(18) | TRP(24) | TRP(22) | TRP(19) | TRP(8) | TRP(19) |
| 105 | GLN(5) | | | | | | | | | | |

The buried, inward-pointing FR amino acids in the $V_L$ domains, i.e., those which are located in the domain interior, are listed in Table 5 below.

TABLE 5

Inward-Pointing, Buried Framework Residues in the $V_L$ of Fabs of Known Three-Dimensional Structure

| | ANTIBODY | | | | | | | | | | |
|---|---|---|---|---|---|---|---|---|---|---|---|
| POSITION | J539 | McPC603 | HyHEL-10 | HyHEL-5 | R19.9 | 4-4-20 | 36-71 | B13I2 | D1.3 | NEWM | KOL |
| 2 | ILE | ILE | ILE | ILE | ILE | VAL | ILE | VAL | ILE | | |
| 4 | LEU | MET | LEU | LEU | MET | MET | MET | MET | MET | LEU | LEU |
| 6 | GLN | GLN | GLN | GLN | GLN | GLN | GLN | GLN | GLN | GLN | GLN |
| 11 | THR | LEU | LEU | MET | LEU | LEU | LEU | LEU | LEU | VAL | ALA |
| 13 | ALA | VAL | VAL | ALA | ALA | VAL | ALA | VAL | ALA | | |
| 19 | VAL | VAL | VAL | VAL | VAL | ALA | VAL | ALA | VAL | VAL | VAL |
| 21 | ILE | MET | LEU | MET | ILE | ILE | ILE | ILE | ILE | ILE | ILE |
| 23 | CYS | CYS | CYS | CYS | CYS | CYS | CYS | CYS | CYS | CYS | CYS |
| 35 | TRP | TRP | TRP | TRP | TRP | TRP | TRP | TRP | TRP | TRP | TRP |
| 37 | GLN | GLN | GLN | GLN | GLN | LEU | GLN | LEU | GLN | GLN | GLN |
| 47 | TRP | LEU | LEU | TRP | LEU | LEU | LEU | LEU | LEU | LEU | LEU |
| 48 | ILE | ILE | ILE | ILE | VAL | ILE | ILE | ILE | VAL | | ILE |
| 49 | | | | | | | | | | PHE | |
| 58 | VAL | VAL | ILE | VAL | VAL | VAL | VAL | VAL | VAL | | VAL |
| 61 | ARG | ARG | ARG | ARG | ARG | ARG | ARG | ARG | ARG | | ARG |
| 62 | PHE | PHE | PHE | PHE | PHE | PHE | PHE | PHE | PHE | PHE | PHE |
| 71 | TYR | PHE | PHE | TYR | TYR | PHE | TYR | PHE | TYR | ALA | ALA |
| 73 | LEU | LEU | LEU | LEU | LEU | LEU | LEU | LEU | LEU | LEU | LEU |
| 75 | ILE | ILE | ILE | ILE | ILE | ILE | ILE | ILE | ILE | ILE | ILE |
| 78 | MET | VAL | VAL | MET | LEU | VAL | LEU | VAL | LEU | LEU | LEU |
| 82 | ASP | ASP | ASP | ASP | ASP | ASP | ASP | ASP | ASP | ASP | ASP |
| 83 | | | | | | | | | PHE | | |
| 84 | ALA | ALA | | ALA | ALA | | ALA | | | ALA | THR |
| 86 | TYR | TYR | TYR | TYR | TYR | TYR | TYR | TYR | TYR | TYR | TYR |
| 88 | CYS | CYS | CYS | CYS | CYS | CYS | CYS | CYS | CYS | CYS | CYS |
| 102 | THR | THR | THR | THR | THR | THR | THR | THR | THR | THR | THR |
| 104 | LEU | LEU | LEU | LEU | LEU | LEU | LEU | LEU | LEU | LEU | LEU |
| 106 | LEU | ILE | ILE | ILE | | | ILE | ILE | | VAL | VAL |

Those in the $V_H$ domain are listed in Table 6 below.

TABLE 6

Inward-Pointing, Buried Framework Residues in the $V_H$ of Fabs of Known Three-Dimensional Struture

| | ANTIBODY | | | | | | | | | | |
|---|---|---|---|---|---|---|---|---|---|---|---|
| POSITION | J539 | McPC603 | HyHEL-10 | HyHEL-5 | R19.9 | 4-4-20 | 36-71 | B13I2 | D1.3 | NEWM | KOL |
| 2 | VAL | VAL | VAL | | | | VAL | VAL | VAL | | VAL |
| 4 | LEU | LEU | LEU | LEU | LEU | LEU | LEU | LEU | LEU | LEU | LEU |
| 6 | GLU | GLU | GLU | GLN | GLU | GLU | GLN | GLU | GLU | GLN | GLN |
| 9 | | | PRO | | | | | | | | |
| 12 | VAL | VAL | VAL | MET | VAL | VAL | VAL | VAL | VAL | VAL | VAL |
| 18 | LEU | LEU | LEU | VAL | VAL | MET | VAL | LEU | LEU | LEU | LEU |
| 20 | LEU | LEU | LEU | ILE | MET | LEU | MET | LEU | ILE | LEU | LEU |
| 22 | CYS | CYS | CYS | CYS | CYS | CYS | CYS | CYS | CYS | CYS | CYS |
| 24 | ALA | THR | VAL | ALA | ALA | ALA | ALA | ALA | VAL | VAL | SER |
| 27 | PHE | PHE | ASP | TYR | TYR | PHE | TYR | PHE | PHE | THR | PHE |
| 29 | PHE | PHE | ILE | PHE | PHE | PHE | PHE | PHE | LEU | PHE | PHE |
| 36 | TRP | TRP | TRP | TRP | TRP | TRP | TRP | TRP | TRP | TRP | TRP |
| 38 | ARG | ARG | ARG | LYS | LYS | ARG | LYS | ARG | ARG | ARG | ARG |
| 40 | | | | | | SER | | | | | |
| 46 | | GLU | GLU | GLU | | | | | | | |
| 48 | ILE | ILE | MET | ILE | ILE | VAL | ILE | VAL | LEU | ILE | VAL |
| 49 | | ALA | | | | ALA | | ALA | | | ALA |
| 66 | LYS | ARG | ARG | LYS | | | | ARG | ARG | ARG | ARG |
| 67 | PHE | PHE | ILE | ALA | THR | PHE | THR | PHE | LEU | VAL | PHE |
| 69 | ILE | VAL | ILE | PHE | LEU | ILE | LEU | ILE | ILE | MET | ILE |
| 71 | ARG | ARG | ARG | ALA | VAL | ARG | VAL | ARG | LYS | VAL | ARG |
| 76 | | | | | | SER | | | | | |
| 78 | LEU | LEU | TYR | ALA | ALA | VAL | ALA | LEU | VAL | PHE | LEU |
| 80 | LEU | LEU | LEU | MET | MET | LEU | MET | LEU | LEU | LEU | LEU |
| 82 | MET | MET | LEU | LEU | LEU | MET | LEU | MET | MET | LEU | MET |
| 82C | VAL | LEU | VAL | LEU | LEU | LEU | LEU | LEU | LEU | VAL | LEU |
| 86 | ASP | ASP | ASP | ASP | ASP | ASP | ASP | ASP | ASP | ASP | ASP |
| 88 | ALA | ALA | ALA | | ALA | | ALA | ALA | ALA | ALA | |
| 90 | TYR | TYR | TYR | TYR | TYR | TYR | TYR | TYR | TYR | TYR | TYR |
| 92 | CYS | CYS | CYS | CYS | CYS | CYS | CYS | CYS | CYS | CYS | CYS |
| 94 | ARG | ARG | ASN | HIS | ARG | | ARG | ARG | ARG | ARG | ARG |
| 107 | THR | THR | | THR | THR | THR | THR | THR | THR | SER | THR |
| 109 | VAL | VAL | VAL | LEU | LEU | VAL | LEU | LEU | LEU | VAL | VAL |
| 111 | VAL | VAL | VAL | VAL | VAL | VAL | VAL | VAL | VAL | VAL | VAL |

From the above, it may be seen that (1) There are many FR amino acids that either contact the CDRs or the opposite domain, or are found in the domain interior.

(2) These FR amino acids, which could influence the structure of the combining site, and thus the antigen-binding characteristics of an antibody, are different from antibody to antibody.

It is obvious from these results that no one structure can serve as the perfect and sole basis of all humanization protocols. In fact, to "humanize" the 9 murine antibodies shown Table 1 above the CDR-grafting with a view to preserving their ligand-binding properties, the FR amino acids listed in Table 2 to 6 above would have to be retained.

A search through the tables of immunoglobulin sequences (Kabet et al., "Sequences of Proteins of Immunological Interest", 5th Ed., US Dept. of Health and Human Service, NIH Publication No. 91-3242 (1991)), shows that human variable domain sequences are known that already have most of the FR amino acids that need to be preserved as shown in Table 7 below.

TABLE 7

Human Antibodies that are Most Similar in Sequence to Murine Antibodies of Known Three-Dimensional Structure

| ANTIBODY | DOMAIN | MOST SIMILAR HUMAN SEQUENCE |
|---|---|---|
| HyHEL-10 | VH | 58P2'CL (77/112) |
| | VH FRAMEWORK | 15P1'CL, ML1'CL (62/87) |
| | VH IMPT | 58P2'CL, Ab26'CL, C6B2'CL (28/38) |
| | VL | IARC/BL41'CL (73/107) |
| | VL FRAMEWORK | IARC/BL41'CL (59/80) |
| | VL IMPT | IARC/BL41'CL (30/37) |
| HyHEL-5 | VH | ND'CL (74/116) |
| | VH FRAMEWORK | 783c'CL, X17115'CL (63/87) |
| | VH IMPT | 21/28'CL, 51P1'CL, 783c'CL, 8E10'CL, AND, KAS, NEI'CL, X17115'CL (25/37) |
| | VL | HF2-1/17'CL, KAS (65/105) |
| | VL FRAMEWORK | HF2-1/17'CL (57/80) |
| | VL IMPT | BI, DEN, HF2-1/17'CL, KUE, REI, WALKER'CL, WIL (=) (27/36) |

| | | |
|---|---|---|
| R19.9 | VH | 21/28'CL (73/119) |
| | VH FRAMEWORK | 21/28'CL, 51P'CL, AND, LS2'CL, NEI'CL, (60/87) |
| | VH IMPT | 21/28'CL, 8E10'CL, Ls2'CL (28/38) |
| | VL | WALKER'CL (78/107) |
| | VL FRAMEWORK | RZ (62/80) |
| | VL IMPT | REI, WALKER'CL (33/36) |
| 4-4-20 | VH | 30P1'CL (77/116) |
| | VH FRAMEWORK | 2P1'CL, 3D6'CL (65/87) |
| | VH IMPT | 4B4'CL, M26'CL (36/41) |
| | VL | RPM1-6410'CL (91/112) |
| | VL FRAMEWORK | GM-607-'CL (68/80) |
| | VL IMPT | CUM, FR, NIM (33/26) |
| J539 | VH | 30P1'CL, Vh38CL, 10'CL (81/118) |
| | VH FRAMEWORK | 18/2'CL, 30P1'CL, M43 (71/87) |
| | VH IMPT | 38P1'CL, 56P1'CL, M72, M74 (36/40) |
| | VL | PA (62/105) |
| | VL FRAMEWORK | LEN, WEA, (53/80) |
| | VL IMPT | BI, DEN, KUE, REI, WALKER'CL, WIL (=) (26/35) |
| McPC603 | VH | M72 (81/120) |
| | VH FRAMEWORK | 4G12'CL, Ab18'CL, M72 (70/87) |
| | VH IMPT | 56P1'CL, M72, M74, RF-SJ2'CL (36/42) |
| | VL | FK-001'CL, LEN (91/113) |
| | VL FRAMEWORK | LEN (70/80) |
| | VL IMPT | LEN (38/42) |
| 36-71 | VH | 21/28'CL (74/119) |
| | VH FRAMEWORK | 21/28'CL, 51P1'CL, 783c'CL, AND'CL, NEI'CL, X17115'CL, (61/87) |
| | VH IMPT | 21/28'CL, 8E10'CL (28/38) |
| | VL | AG (76/105) |
| | VL FRAMEWORK | RZ (63/80) |
| | VL IMPT | REI, RZ, WALKER'CL (34/37)' |
| B13I2 | VH | 56P1'CL (83/119) |
| | VH FRAMEWORK | 4B41CL, 4G12'CL, M26'CL, M72, RF-SJ2'CL, Vh38Cl.10'CL (68/87) |
| | VH IMPT | 56P1'CL, M72, M74, RF-SJ2'CL (37/39) |
| | VL | RPM1-6410'CL (86/112) |
| | VL FRAMEWORK | GM-607-'CL (69/80) |
| | VL IMPT | CUM, NIM (36/39) |
| D1.3 | VH | C6B2'CL (72/116) |
| | VH FRAMEWORK | C6B2'CL (62/87) |
| | VH IMPT | M60'CL (32/37) |
| | VL | BR (75/107) |
| | VL FRAMEWORK | HF2-1/17'CL (64/80) |
| | VL IMPT | 3D6'CL, BI, DEN, EU, KUE, PA, REI, WALKER'CL, WIL (=) (32/36) |

These human sequences are not necessarily those which are most similar to the murine antibodies, overall or in the framework regions only, but rather, those that possess the largest number of important amino acids in common, the latter sequences being included in Table 7 above.

The number of murine amino acids that still need to be retained in order to have all the important FR amino acids in the "humanized" versions of the murine antibodies as shown in Table 7 above, ranges from 21 (for HyHEL-5:12 in $V_H$ and 9 in $V_L$) to 5 (for B1312:2 in $V_H$ and 3 in $V_L$). These are not very many amino acids, considering that the resulting humanized molecules will probably retain most or all their ligand-binding characteristics. It is possible that there exist other human sequences that are even more similar to these murine domains that are not included in the compilation of Kabat, et al. (1991), supra. When more sequences become available these may also be incorporated to improve the pool of basic data available for use in the humanization of antibodies.

b) Choosing the best human framework to use in the "humanization" of an antibody when its structure is not known.

In the absence of a three-dimensional structure, the identification of the FR amino acids that are crucial to maintain the combining site structure is not easily done. Nevertheless, some proposals may be made from the data shown in Table 2 to 6 above that have been collected in Tables 8 and 9 below for the $V_L$ and $V_H$ domains.

TABLE 8

Framework Residues in $V_L$ That Probably Need To Be Preserved in Order to Reproduce the Ligand Properties of the Original Antibody

| | | | CDR1 | |
|---|---|---|---|---|
| J539 | EI.L.Q.... | T.A.....V.I.C | sass-------svsslh | WYQQ.....SP.PWIY |
| McPC603 | DIVMTQ.... | L.V.....V.M.C | rssgsllnsqnqknfla | WYQQ.....PP.LLIY |
| HyHEL-10 | DIVL.Q.... | L.V.....V.L.C | rasq------signnlh | WYQQ.....SP.LLIK |
| HyHEL-5 | DIVL.Q.... | M.A.....V.M.C | sass-------svnymy | WYQQ.....SP.RWIY |
| R19.9 | .IQMTQ.... | L.A.....V.I.C | rasq------disnyln | WYQQ.....T.KLLVY |
| 4-4-20 | DVVMTO.... | L.V.....A.I.C | rasq-slvbsqqntylr | WYLQ.....PKVLIY |
| 36-71 | DIQM.Q.... | L.A.....V.I.C | rasq------dinnfln | WYQQ.....I.LLIY |
| B13I2 | .VLM.Qr... | L.V.....A.ISC | ranq-tillsdgdtyle | WYLQ.....SP.LLIY |
| D1.3 | DI.M.Q.... | L.A.....V.I.C | rasq------nihnyla | WYQQ.....SP.LLVY |
| | CDR2 | | | CDR3 |
| J539 | eisklas | .V..RF.....Y.L.I..M...D.A.YYC | | qqwtyplit F...T.L.L. |
| McPC603 | gastres | .V.DRF....S.TDF.L.I..V...D.A.YYC | | qndhsyplt F.A.T.L.I. |
| HyHEL-10 | yasqsis | .I..RF.....T.F.L.I..V...D..MYPC | | qqsnswpyt F...T.L.I. |
| HyHEL-5 | dtsklas | .V..RF.....Y.L.I..M...D.A.YYC | | qqwqr-npt F...T.L.I. |

TABLE 8-continued

| Framework Residues in $V_L$ That Probably Need To Be Preserved in Order to Reproduce the Ligand Properties of the Original Antibody | | | | |
|---|---|---|---|---|
| R19.9 | ytsrlhs | .V..RF.....DY.L.I..L...D.ATY.C | qqqsttprt | F...T.L... |
| 4-4-20 | kvsnrfs | .V.DRF.....T.F.L.I..V...D...Y.C | sqsthvpwt | F...T.L... |
| 36-71 | ftsrsqs | .V..RF.....TDY.L.I..L...D.A.YFC | cqqnalprt | F...T.L.I. |
| B13I2 | kvsnrfs | .V.DRF.....T.F.L.I..Y...D..VYYC | fqqshwppt | F...T.L.I. |
| D1.3 | ytttlsd | .V..RF....S.T.Y.L.I..L...DF..YYC | qbfwstprt | F...T.L... |

TABLE 9

| Framework Residues in $V_H$ That Probably Need to Be Preserved in Order to Reproduce the Ligand Properties of the Original Antibody | | | | |
|---|---|---|---|---|
| | | | CDR1 | |
| J539 | .V.L.E.....V.....L.L.C.A..FDF. | | kywms | WVRQ.....LEWI. |
| McPC603 | .V.L.E.....V.....L.L.C.T..FTF. | | dfyme | WVRQ....RLEWIA |
| HyHEL-10 | .V.L.E..P..V.....L.L.C.V..D.IT | | sdyws | WIRK...N.LEYM. |
| HyHEL-5 | ...L.Q.....M.....V.I.C.A..YTF. | | dywis | WVKWR....LEWI. |
| R19.9 | .V.L.E.....V.....V.M.C.A..YTFT | | sygvn | WVKW...W..EWI. |
| 4-4-20 | ...L.E.....V.....M.L.C.A..FTFS | | dyvan | WVRQS....LEWVA |
| 36-71 | EV.L.Q.....V.....V.M.C.A..YTF. | | sngin | WVKQ.....LEWI. |
| B13I2 | .V.L.E.....V.....L.L.C.A..FTF. | | rcams | WVRQ...K.L.WVA |
| D1.3 | .V.L.E.....V.....L.I.C.V..F.L. | | gygvm | WVRQ.....LEWL. |
| | CDR2 | | | |
| J539 | eihp--dsgtinytpslkd | KF.I.R.N....L.L.M..V...D.A.YYCAR | | |
| McPC603 | asrnkgnkytteysasvkg | RFIV.R.T....L.L.M..L...D.A.YYCAR | | |
| HyHEL-10 | yvs---ysgstyynpslks | RI.I.R.....Y.L.L..V...D.A.YYC.N | | |
| HyHEL-5 | eilp--gagstnyverfkg | KA.F.A.....A.M.L..L...D...YYCLH | | |
| R19.9 | yinp--gkgylsynekfkg | .TTL.V.....A.M.L..L...D.A.YFC.R | | |
| 4-4-20 | girnkpynystyysdsvkg | RFTI.R.D..S.V.L.M..L...D...YYCT. | | |
| 36-71 | ynnp--gngyiaynekfkg | .T.L.V.....A.M.L..L...D.A.YFCAR | | |
| B13I2 | giss--ggsytyfpdtyag | RF.I.R.....L.L.M..L...D.A.YYCTR | | |
| D1.3 | miv---gdgntdynsalks | RL.I.K.....V.L.M..L...D.A.YYCAR | | |
| | CDR3 | | | |
| J539 | lhygyn-------sy | W.Q.T.V.V.. | | |
| McPC603 | nyygstwyf----dy | W...T.V.V.. | | |
| HyHEL-10 | wdg----------dy | W...T.V.V.. | | |
| HyHEL-5 | gnydf--------dg | W...T.L.V.. | | |
| R19.9 | sfyggsdlavyyfds | W...T.L.V.. | | |
| 4-4-20 | syygm--------dy | W...T.V.V.. | | |
| 36-71 | seyyggsykf---dy | W...T.L.V.. | | |
| B13I2 | yssdpfyf-----dy | W...T.L.V.. | | |
| D1.3 | erdyrl-------dy | W...T.L.V.. | | |

From Tables 8 and 9 above, it may be seen that many of the important FR amino acids flank the CDRs. Among these flanking positions are most of the FR amino acids that are involved in the contact with the opposite domain as shown in Table 4 above, and many of those which are in contact with the CDRs as shown in Tables 2 and 3 above. Moreover, almost all of the FR amino acids that have been observed to participate in the binding to antigen (Amit, A. G. et al., Science 233:747–753 (1986); Sheriff, et al., P.N.A.S. (USA) 82:1104–1107 (1987); Padian, E. A., et al., P.N.A.S. (USA) 86:5938–5942 (1989); Tulip, et al., Cold Spring Harbor Symp. Quant. Biol. 54:257–263 (1989); Bentley, et al., Nature (London) 348: 254–257 (1990)), are in these flanking regions. Thus, during humanization, not just the CDRs are retained, but also some of the residues immediately adjacent to the CDRs. This provides a better chance of retaining more of the ligand-binding properties of the original antibody. The likelihood of retaining the antigen binding properties of the mouse antibody is even greater if the first few amino acids in the $NH_2$-termini of both chains are also retained, since some of them are found to be in contact with CDRs as shown in Tables 2 to 3 above. Further, Tables 8 and 9 above also show many other framework positions that are deemed structurally important in all the case examined here. The murine residues at those positions should probably be retained is well.

Alternatively, it may possible to reduce immunogenicity, while preserving antigen-binding properties, by simply replacing those exposed residues in the framework regions which differ from those usually found in human antibodies (Padlan, E. A. (1991), supra). This would humanize the surface of the anti KC-4 murine antibody while retaining the interior and contacting residues which influence is antigen-binding characteristics. The judicious replacement of exterior residues should have little, or no, effect on the interior of the domains, or on the interdomain contacts. For example, the solvent accessibility patterns of the $F_VS$ of J539, a murine IgA (κ) and of KOL, a human IgG1 (λ) have been found to be very similar (Padian, E. A. (1991), supra).

At the present, more than 35 different Fab structures have been elucidated by X-ray diffraction analysis, although atomic coordinates for only 11 are currently in the Protein Data Bank as shown in Table 1 above. Most of the available structures have been analysed to only medium resolution, some having been refined to only a limited extent. Eventually, atomic coordinates for more and better-refined structures will become available, so that the "important" FRs will be more easily assessed. This will improve the theoretical predictive record of the present method for determining the sequence of the humanized antibodies.

The design of the humanized anti-KC-4 murine antibody is reached in stages as follows.

1—Choice of a murine model of known structure.

2—Choice of the human FR.

3—Identification of murine/human antibody differences.

4—Identification of important murine amino acids.

1) Choice of a xenogeneic model of known structure

The $V_H$ and $V_L$ domains of an antibody of desired specificity are classified according to Kabat et al.(1991), supra. Then, another human antibody may be chosen, whose structure has been determined, and whose variable regions belong to the same classes and subclasses. Modeling the murine antibody in question to such structure ensures maximal chance for success. This, however, is not absolutely necessary since the relative positions of the important amino acids do not vary considerable even in variable regions of different classes. Thus, with less than a perfect match, this method has been applied to design the humanized anti-KC-4 antibodies of this invention. Once the murine model is chosen, it may be applied to identify the locations of important residues in the murine antibody to be humanized. Tables 2, 3, 4, 5, 6, 8 and 9 indicate the positions of the important amino acids in several antibodies whose structures have been determined to a high resolution level.

(2) Choice of the target species FR

The target species framework should, ideally, be consensus framework. That is, one that has a maximum number of amino acids in common with all human frameworks of the same class. This is important, because, the goal of humanization is to avoid an immunological response against the engineered humanized anti-KC-4 antibody.

The target species framework that is chosen is that which shares the greatest number of important amino acids with the original murine antibody. Thus, in choosing the human FRs, the similarity between the important amino acids is more important that the overall similarity.

In practice, the sequences of the murine variable chains were aligned with the consensus sequences from all variable region classes of the anti-KC-4 murine antibody and the number of differences in the amino acids that must be retained from the murine antibody were scored. The human consensus sequence(s) that score(s) the lowest number of differences is (are) then chosen. These are the best antibody candidates. Others with low numbers that are higher than the above may also be suitable, and are placed in a reserve pool, and so forth. If there are too many differences in the chosen framework (e.g., more than 16), then the same alignment procedure using all tabulated human sequences may be repeated in order to find a specific human framework whose similarity with the murine sequence is maximized at the positions of the important amino acids. Thus, most preferably, the target species FR should be a consensus sequence. Next preferable would be a framework of a common human antibody, and finally, the framework of any human antibody.

(3) Identification of murine/human antibody differences

The murine sequences are then aligned with the human sequences and the position of all amino acids that differ in the murine and in the human frameworks are tabulated. Such a table contains the maximum number of amino acids that can be changed towards the humanization of the anti KC-4 murine antibody (see, Table 19 below). If all those changes were to be made, a so-called CDR-grafted antibody would be obtained. That is, only the original CDRs would be retained from the anti-KC-4 murine antibody. The affinity of a CDR-grafted antibody by itself would be considerably less than that of the original anti-KC-4 murine antibody. In order to maximize the chances for conserving the original affinity, the identities of all important amino acids must be preserved.

(4) Identification of important murine amino acids

In the first step towards humanizing an antibody, the amino acids that are correspondingly important in the anti-KC-4 murine antibody chosen in step 1 are retained. In a subsequent step, however, the amino acids that have been shown to occupy important positions in other murine antibodies or in human antibodies may also be retained and are therefore taken out from the group of candidates to be mutated. The second step is particularly appropriate if all chances that the amino acids in question could make contacts with the CDRs or with the opposite chains are to be avoided. Once the important murine amino acids are identified, the DNA sequence may be mutagenized to change all other amino acids, which for the most part occupy exposed positions.

The present method was applied in the exemplary disclosure provided hereinbelow to the humanization of the anti-KC-4 murine antibody starting from a chimeric antibody consisting of anti-KC-4 mouse variable regions and human constant regions. Murine and human antibodies, whose three-dimensional structures have been deduced to a high degree of resolution, were utilized as guidance in the choice of the amino acids to be substituted in order to humanize this murine antibody. Information on other murine antibodies from a Data Bank was used in the exemplary disclosure provided below to modify the anti-KC-4 murine-human chimeric antibodies with human amino acids.

The cDNAs encoding the anti-KC-4 humanized variable regions were then cloned into a vector containing sequences encoding constant regions of a human antibody placed under the same promoter. Although this is the cloning strategy utilized in the exemplary disclosure of this invention, other methods known in the art may also be utilized such as co-expression and the like. In the exemplary disclosure provided herein, the anti-KC-4 murine-human chimeric antibodies were considered by joining the DNAs of the anti-KC-4 murine variable domain to a human constant domain (an effector agent) cloned into a hybrid vector, and the product expressed by transfecting the vector into myeloma cells. The variable regions of the chimeric antibodies were then modified at the DNA level to obtain the humanized chimeric antibodies. The modifications to the variable regions of the peptides may either be conducted by PCR amplification with primers that are custom tailored to produce the desired mutations, or by DNA synthesis.

The anti-KC-4 humanized antibodies exemplified below comprises the humanized variable regions of the anti-KC-4 murine/human chimeric antibody (U.S. Pat. No. 4,708,930 to Coulter discloses the anti-KC-4 mouse antibody technology) and the kappa and gamma 1 constant region of a human antibody. These human antibodies were characterized by their molecular weight and binding specificities, and shown to complete well with, or better than, the corresponding murine and chimeric antibodies for the KC-4 antigen. The humanized antibodies were shown to bind weakly to normal breast, lung, colon and endometrium, and strongly to carcinoma tissue sections by the ABC immunoperoxidase method. The portions of the CDR and FR regions of the non-modified peptides (murine $F_V$ regions) and effector agents (human $F_C$ regions) were shown in both cases to be substantially identical to those of the murine and human antibodies from which they were obtained. The anti-KC-4 humanized antibodies of this invention lacking any non-human constant region sequences possess less foreign antigenic epitopes than the whole murine or chimeric antibodies from which they were derived. Accordingly, they are expected to elicit a less complex immunogenic response in humans than the corresponding whole murine antibodies and even than the murine/human chimeric antibodies. However, to what extent a portion of the murine FR amino acids may be replaced without altering the binding characteristics of the CDRs could not have been predicted prior to this invention because of the substantial conformational alterations in the interior regions that affect the binding of the CDRs to the antigen that may occur upon modification of amino acid sequences.

Thus, the substantially pure, isolated anti-KC-4 humanized antibody of the invention specifically and selectively binds to the human KC-4 antigen described in U.S. Pat. No. 4,708,930. The antibody consists of a light and a heavy chain consisting essentially of the variable region of the light and heavy chains of the anti-KC-4 murine antibody having the FRs substituted with seven amino acids for the light chain and twelve amino acids for the heavy chain present in equivalent positions in antibodies of other species, and the constant regions of a human antibody.

The humanization procedure described here is designed to minimize potential losses in antigen binding affinity that may result from the introduced amino acids. In the case of the anti-KC-4 humanized antibody described herein, seven amino acid changes were introduced in the variable region of the light chain and twelve amino acid changes were made in the variable region of the heavy chain. Furthermore, to minimize the immunological response to the humanized antibody, target human amino acid sequences were used that comprise the consensus sequences of all appropriate human variable regions. In one particularly preferred embodiment of the invention the anti-KC-4 humanized antibody consists essentially of the amino acid sequence ID No. 50 of Table 24 and/or the sequence ID No. 51 of Table 25.

The present anti-KC-4 humanized monoclonal antibodies are provided either as a naked peptide or in glycosylated form. When provided in glycosylated form, the antibodies are attached to a glycosyl residue(s) provided by the eukaryotic cell where it is expressed. When cloned and expressed in a prokaryotic cell it is provided as the naked polypeptide, and the glycosyl residue(s) may be added thereafter, for example by means of glycosyl transferases as is known in the art.

The anti-KC-4 humanized antibodies of this invention may also be added a radioisotope by methods that are known in the art.

In a most preferred embodiment, the anti-KC-4 humanized antibody comprises the humanized antibody expressed by the [hybridoma] cell line having the ATCC Accession No. HB 11,455 (HuKC-4V2), deposited under the Budapest Treaty on Sep. 23, 1993. This [hybridoma] *cell line* was deposited as the best mode of the invention known to the inventors.

The anti-KC-4 humanized antibodies of the invention are also provided as a composition along with a carrier or diluent for use in vitro, preferably a pharmaceutically-acceptable carrier or diluent for use in vivo and ex vivo. The anti-KC-4 humanized antibody provided herein may be present in the composition in an amount of about 0.001 to 99.99 wt %, more preferably about 0.01 to 20 wt %, and still more preferably about 1 to 5 wt %. However, other amounts are also suitable. Carriers generally, and pharmaceutically-acceptable carriers in particular, are known in the art and need not be further described herein. The carrier may be provided in a separate sterile container or in admixture with the antibody. Typically, saline, aqueous alcoholic solutions, albumin-saline solutions, and propylene glycol solutions are suitable. However, others may also be utilized. When utilized for therapeutic purposes the proteic material must be of a purity suitable for human administration, and the composition may contain other ingredients as is known in the art. Examples of these are other anti-neoplastic drugs such as adriamycin and mitomycin, cytoxan, PALA and/or methotrexate, among others. However, other therapeutic drugs, carriers or diluents, immunological adjuvants and the like may be also be added. When the composition described above is utilized for in vivo imaging, it may comprise about 0.001 to 99.9 wt % humanize antibody, and more preferably about 0.01 to 25 wt % humanized antibody. Typically, when the composition is utilized for therapeutic purposes it may contain about 0.001 to 99.9 wt % humanized antibody, and more preferably about 0.01 to 30 wt % humanized antibody. When utilized for the ex vivo purging of neoplastic cells from bodily fluids such as spinal fluid, the composition may comprise about 0.0001 to 50 wt %, and preferably about 0.01 to 20 wt % humanized antibody. When applied to the in vitro diagnosis of carcinomas the composition of the invention may comprise about 0.001 to 35 wt % humanized antibody, and more preferably about 0.01 to 10 wt % humanized antibody. Other amounts, however, are also suitable.

Such products find one utility in the treatment of cancer, such as breast, lung, ovary, endometrial, pancreas, prostate and colon cancers, among others. The anti-KC-4 humanized antibodies may be used for the in vivo treatment of diagnosis of humans. The present analogue peptides are particularly suitable for repeated administration to humans and for long term therapy, such as is the case of metastases, and/or the reoccurrence of tumors.

A kit for the diagnosis of cancer cells provided herein comprises the anti-KC-4 humanized antibody of the invention, and instructions for its use, and optionally a positive control, and heterologous immunoglobulins selectively binding the constant regions of the antibody, protein G or protein A. The diagnostic kit may also be provided with a radiosotope or a fluorescent label.

A cancer patient may be imaged in vivo and/or diagnosed by administration of the anti-KC-4 humanized antibody of the invention in radiolabeled form, in an amount effective to reach the locus of the cancer and bind to the cancer cells, and further non-invasive detection of any localized binding of the labeled anti-KC-4 humanized antibody to the tumor cells. Typically, the anti-KC-4 humanized antibody may be administered in an amount of about 0.001 to 5000 mg/kg weight per treatment, more preferably about 0.01 to 5000 μg/kg weight per treatment, and more preferably about 0.1 to 500 μg/kg weight per treatment. However, other amounts may also be utilized. Radiolabels that may be utilized are $^{111}$In, $^{125}$I, $^{99m}$Tc, and $^{131}$I, among others. These radiosotopes may be detected with a PET scanner, and with an NMR imaging and/or radioactivity counting apparatus that are in wide use by the medical community, depending on the radiolabel utilized.

A cancer may be diagnosed in vitro by contacting a biological sample with the anti-KC-4 humanized antibody described here into form an anti-KC-4 humanized antibody-cancer cell antigen complex with any cancer or cancer-associated cell antigen present in the sample, and detecting any complex formed. The biological sample is typically obtained from a human suspected of being afflicted with cancer. Suitable biological samples are serum blood, sputum, feces, lymph fluid, spinal fluid, lung secretions, and urine, among others. Clearly, any source of fluid, tissue and the like may be prepared for use in this method as is known in the art.

The anti-KC-4 humanized antibody of this invention was shown to have tissue specificities similar to that of the anti-KC-4 murine antibody. The anti-KC-4 humanized monoclonal antibody was shown to bind specifically and strongly to solid tumor tissue in the lung, colon, kidney, breast, stomach, prostate, pancreas, lymph node duct and lymphoma, and non-specifically and weakly to normal breast, kidney, and stomach tissue. The anti-KC-4 murine antibody also showed some weak binding to normal tissue including spinal cord, uterus, thyroid, tongue, prostate, spleen, adrenal, lung, gall bladder, heart, lymph nodes, colon, liver, brain, testes, thymus, and placenta (U.S. Pat. No. 4,708,930).

The present anti-KC-4 humanized antibodies are also applicable to the purging of cancer cells from biological samples, be it fluid or tissue samples. The purging of neoplastic cells from a fluid sample is part of the invention and may be practiced by contacting a biological fluid suspected of comprising neoplastic cells with the anti-KC-4 humanized antibody of the invention, and allowing the antibody to bind to any KC-4-related antigen present on the cells, and separating the anti-KC-4 humanized antibody cell complex from the remainder of the fluid.

This method may be utilized for purging unwanted cell ex vivo by extracting a biological sample from a patient, eliminating the neoplastic cells therefrom by separation of the anti-KC-4 humanized antibody-cell complexes or by further addition of an effector such as complement or a toxin or a radioactive label that can act upon the cell and then replenishing the purged sample to the patient. This is typically suitable for use with spinal taps where spinal fluid is rid of carcinoma cells prior to reinjection. Other fluids may also be treated in this manner.

The present humanized antibodies may also be applied to the histochemical assessment of the presence of cancer cells in a tissue obtained from a subject suspected of begin afflicted with cancer by methods that are standard in the art, like the preparation of tissue slices and their fixation on a solid substrate to permit the application of the monoclonal antibody of the invention, and then the assessment of any binding to neoplastic cells in the sample as indicated by the formation of complexes between the anti-KC-4 humanized antibody and antigens to which it selectively binds on the cells.

The growth or the size of a primary or metastasized cancer may be inhibited or reduced by administering to a subject in a need of the treatment an effective amount of the anti-KC-4 humanized antibody of the invention in radiolabeled form. Typically, the monoclonal antibody provided herein may be administered in an amount of about 0.001 to 2000 mg/kg body weight per does, and more preferably about 0.01 to 500 mg/kg body weight per dose. Repeated doses may be administered as prescribed by the treating physician. However, other amounts are also suitable. Generally, the administration of the antibody of the invention is conducted by infusion so that the amount of radiolabel present that may produce a detrimental effect may be kept under control by varying the rate of administration. Typically, the infusion of one dose may last a few hours. However, also contemplated herein is the constant infusion of a dose for therapeutic purposes that will permit the maintenance of a constant level of the antibody of this invention in serum. The infusion of the monoclonal antibody of the invention may be conducted as follows. Intravenous (I.V.) tubing may be pretreated, e.g., with 0.9% NaCl and 5% human serum albumin and placed for intravenous administration. The prescribed dose of the analogue peptide may be infused as follows. Unlabeled analogue peptide may be infused initially. 30 minutes after completion of the unlabeled antibody infusion. $^{111}$In-labeled and $^{90}$Y labeled antibody may be con-infused. The I.V. infusion may comprise a total volume of 250 ml of 0.9% NaCl and 5% human serum albumin and be infused over a period of about 2 hours depending on any rate-dependent side effects observed. Vital signs should be taken, e.g., every 15 minutes, during the infusion and every one hour post infusion until stable. A thorough cardiopulmonary physical examination may be done prior to, and at the conclusion, of the infusion. Medications including acetaminophen, diphenhydramine, epinephrine, and corticosteroids may be kept at hand for treatment of allergic reactions should they occur. The administration of the hybrid analogue peptide of practitioner. Typically, once a first dose has been administered and imaging indicates that there could be a reduction in the size of the tumor, whether primary of metastasized, repeated treatments may be administered every about 1 to 100 days, and more preferably every about 2 to 60 days. up to about 2 years, and in some circumstances even for longer periods of time or until complete disappearance of the tumor(s). The administration of the radiolabeled antibody of this invention is typically more useful for therapeutic purposes when a primary tumor has, for example, been excised. Thus, it is primarily intended for "mopping-up" therapy after surgical intervention or for applications in cases of cancerous metastases. It is in these cases that the present method is of greatest utility.

A pure, isolated polydeoxyribonucleotide that encodes the anti-KC-4 humanized antibody of this invention may be applied to the preparation of the monoclonal antibody of this invention. In one preferred embodiment, the polydeoxyribonucleotide of the invention consists essentially of a DNA sequence selected from the group consisting of DNA sequence ID Nos. 48 and/or 49 of Tables 21 and 22. These DNA sequences may be cloned for expression under the same promoter.

Also provided herein is a hybrid vector that comprises a vector carrying the polydeoxyribonucleotide of this invention operatively linked thereto. Typically, vectors capable of replication both in eukaryotic and prokaryotic cells are suitable. When the preparation a glycosylated analogue polypeptide is desired the vector should be suitable for transfection of eukaryotic host cells.

This invention also encompasses a host cell that has been transfected with the hybrid vector described above. Suitable hosts are prokaryotic and eukaryotic hosts such as bacteria, yeast, and mammalian cells such as insect cells and non-producing hybridoma cells, among others. Suitable vectors and/or plasmids for the transfection of each one of these types of hosts are known in the art and need not be further described herein. Also known in the art are methods for cloning DNA sequences into each one of these types of vectors and for transfecting the different types of host cells. Particularly preferred is the cell line having the ATCC Accession No. HB 11,455 (HuKC4V2).

Polyribonucleotides may be obtained by transcription of the polydeoxyribonucleotides described above as is known in the art. Provided herein are polyribonucleotides consisting essentially of oligoribonucleotides encoding the variable regions of the anti-KC-4 humanized antibody and the constant regions of a human antibody. The polyribonucleotides may be prepared by cloning the desired DNA segments and then transcribing the thus obtained hybrid polydeoxyribonucleotide into the corresponding RNA sequences.

The anti-KC-4 humanized antibody of the invention may be produced by cloning the polydeoxyribonucleotide encoding the antibody of the invention into a vector to form a hybrid vector, transfecting a host cell with the hybrid vector and allowing the expression of the anti-KC-4 humanized antibody, and isolating the antibody from the cell culture mixture. The DNA segment encoding the anti-KC-1 humanized antibody may be obtained by chemical synthesis or by the site-specific modification of the DNA sequence encoding the variable region of the anti-KC-4 murine or murine-human chimeric antibody by PCR amplification with specifically designed primers as is known in the art. Preferably, the cloning and transfection steps are conducted by cloning polydeoxyribonucleotides encoding the variable region of the heavy or light chains of the anti-KC-4 murine antibody into a DNA segment carrying the genes for the human constant regions, and allowing the antibody chains to be expressed. The expressed antibody chains may then be allowed to interact with one another to form the double chain antibody modified as described above.

Having now generally described this invention, the same will be better understood by reference to certain specific examples, which are included herein for purposes of illustration only and are not intended to be limiting of the invention or any embodiment thereof, unless so specified.

EXAMPLES

Example 1

Methods Utilized

The procedures utilized herein for the reverse-transcription (RT) of RNAs encoding the variable regions and the subsequent amplification of the cDNAs by the polymerase chain reaction (PCR) have been described (Orlandi, R., et al., "Cloning Immunoglobulin Variable Domains for Expression by the Polymerase Chain Reaction", PNAS (USA) 86:3833–3837 (1989); Coloma, M. J., et al., "Primer Design for the Cloning of Immunoglobulin Heavy-Chain Leader-Fvs from Murine Hybridoma Cells Using the PCR", Bio. Techniques 11:152–156 (1991); Gavilondo-Cowley, J. V., et al., "Specific Amplification of Rearranged Immunoglobulin Fv Genes from Murine Hybridoma Cells", Hybridoma 9:407–417 (1990)).

Total RNA is an adequate substrate for RT-PCR. Polyadenylated RNA was utilized herein however, because it contains only minor levels of contaminating ribosomal RNA and practically no DNA. The polyadenylated RNA was isolated with a Fast Track mRNA isolation kit (Invitrogen Corporation, Sand Diego, Calif.).

The oligonucleotides were synthesized on a PCR-Mate EP DNA synthesizer model 391 (Applied Biosystems, Foster City, Calif.). A PCR murine Ig primer set was purchased from Novagen (Madison, Wis.), and complementary DNA (cDNA) was prepared with an RNA PCR kit (Perkin Elmer-Cetus, Norwalk, Conn.).

PCR DNA fragments were cloned directly into pCR1000, using a TA cloning kit (Invitrogen Corporation, San Diego, Calif.) Plasmid DNA was isolated with a kit purchased from Qiagen (Tchapsworth, Calif.), and DNA sequencing was conducted with a Sequenase 2.0 DNA sequencing kit (United States Biochemical, Cleveland, Ohio) using aqueous 5'$\alpha$-$^{35}$SdATP at 600 mCi/mmol (Amersham Corporation, Arlington Heights, Ill.).

Sequence analyses were performed on a Macintosh computer using the program GeneWorks (IntelliGenetics, Inc. Mountain View, Calif.).

Example 2

PCR Primers used in First Isolation of Anti-KC-4 cDNAs

The PCR primers were purchased from Novagen (Madison, Wis.). Their sequences, reproduced from the booklet provided by Novagen, are shown in Table 10 below.

TABLE 10

| PCR Primer Sequences |
|---|
| MulgκV$_L$5'-C: sense primer mix for kappa leader. ACTAGTCGACATGAAGTTGCCTGTTAGGCTGTTGGTGCTG (Seq. ID No: 1) |

TABLE 10-continued

| PCR Primer Sequences |
|---|
| ACTAGTCGACATGGAGWCAGACACACTCCTGYTATGGGT (Seq. ID No: 2) |
| ACTAGTCGACATGGATTTWCAGGTGCAGATTWTCAGCTTC (Seq. ID No: 3) |
| Mulgκ$V_L$3'-1: antisense kappa constant region. |
| CCCAAGCTTACTGGATGGTGGGAAGATGGA (Seq. ID No: 4) |
| Mulg$V_H$5'-F: sense primer mix for heavy chain leader. |
| ACTAGTCGACATGRACTTTGGGYTCAGCTTGRTTT (Seq. ID No: 5) |
| ACTAGTCGACATGAGAGTGCTGATTCTTTTGTG (Seq. ID No: 6) |
| ACTAGTCGACATGGATTTTGGGCTGATTTTTTTTATTG (Seq. ID No: 7) |
| Mulgγ$V_H$3'-2: antisense gamma constant region. |
| CCCAAGCTTCCAGGGRCCARKGGATARACIGRTGG (Seq. ID No: 8) |

Example 3

Amplification of cDNAs Encoding anti-KC-4 Antibody $F_V$ Regions

The cDNAs that encode the anti-KC-4 murine immunoglobulin $V_H$ and $V_L$ were prepared by PCR from polyadenylated RNA isolated from 100 million KC-4 hybridoma cells. All clones were obtained from independent PCRs. The sequences of the primers are given in Example 2 above. Primers are specific for either the leader peptide region or for the constant regions. The primer combinations utilized herein are shown in Table 11 below.

TABLE 11

| Primer Combination for PCR Amplifications | | |
|---|---|---|
| | Clone No. | Primer combinations |
| $V_L$ | 96 | Mulgκ$V_L$5'-C + Mulgκ$V_L$3'-1 |
| | 107 | Mulgκ$V_L$5'-C + Mulgκ$V_L$3'-1 |
| | K1 | JO20 + JO21 |
| $V_H$ | 66 | Mulg$V_H$5'-F + Mulgγ$V_H$3'-2 |
| | 209 | Mulg$V_H$5'-F + Mulgγ$V_H$3'-1 |
| | H3 | JO22 + JO24 |
| | H7 | JO22 + JO24 |

Example 4

Isolation of Amplified anti-KC-4 $V_L$ and $V_H$ cDNA and Sequences

The PCR products were cloned, without prior purification, into pCR1000 (Invitrogen) and sequenced in both directions. The $V_H$ and $V_L$ DNA sequences and their derived protein sequences are shown in Tables 12, 13, 14, and 15 below.

TABLE 12

| $V_L$ Nucleotide sequences anti-KC-4 $V_L$ (kII-Jk2) |
|---|
| ATG AAG TTG CCT GTT AGG CTG TTG GTG CTG ATG TTC TGG ATT CCT GCT TCC AGC AGT GAT GTT TTG ATG ACC CAA ACT CCT CTC TCC CTG CCT GTC AGT CTT GGA GAT CAA GCC TCC ATC TCT TGC AGA TCT AGT CAG AGC ATT GTA CAT AGT AAT GGA AAC ACC TAT TTA GAA TGG TAC CTG CAG AAA CCA GGC CAG TCT CCA AAG CTC CTG ATC TAC AAA GTT TCC ATC CGA TTT TCT GGG GTC CCA GAC AGG TTC AGT GGC AGT GGA TCA GGG ACA GAT TTC ACA CTC AAT ATC AGC AGA GTG GAG GCT GAG GAT CTG GGA ATT TAT TAC TGC TTT CAA GGT TCA CAT GTT CCG TAC ACG TTC GGA GGG GGG ACC AAG CTG GAA ATA AAA C (Seq. ID No: 13) |

TABLE 13

| $V_H$ Nucleotide sequences anti-KC-4 $V_H$ (IIID-D9-JH3) |
|---|
| ATG GAC TTT GGG CTC AGC TTG GTT TTC CTT GTC CTT ATT TTA AAA GGT GTC CAG TGT GAA GTG CAG ATG GTG GAG TCT GGG GGA GTG AAG CCT GGA GGG TCC CTG AAA CTC TCC TGT GCA GCC TCT GGA TTC GCT TTC AGT AGC TAT GCC ATG TCT TGG GTT CGC CAG GAG AAG AGG CTG GAG TGG GTC GCA GAA ATT AGT AGT GGT GGT AAT TAC GCC TAC TAT CAA GAC ACT GTG ACG GGC CGA TTC ACC AGA GAC AAT GCC AAG AAC ACC CTG TAC CTG GAA ATG AGC AGT CTG AGG TCT GAG GAC ACG GCC ATG TAT TAC TGT GCA AGG GAG GGT ATC CCG GCC TGG TTT GCT TAC TGG GGC CAA GGG ACT CTG GTC TCT GTC TCT GAC G (Seq. ID No: 14) |

These cDNA sequences are accurate since in both cases they were identical for clones that were prepared from independent reverse transcription reactions. The derived protein sequences are shown in Tables 14 and 15 below.

TABLE 14

| $V_L$ anti-KC-4 Amino Acid Sequences (kII-Jk2) | |
|---|---|
| | MKLPVRLLVLMFWIPASSS (Seq. ID No: 15) |
| FR1 | DVLMTQTPLSLPVSLGDQASISC (Seq. ID No: 16) |

TABLE 14-continued

| $V_L$ anti-KC-4 Amino Acid Sequences (kII-Jk2) | |
|---|---|
| CDR1 | RSSQSIVHSNGNTYLE (Seq. ID No: 17) |
| FR2 | WYLQKPGQSPKLLIY (Seq. ID No: 18) |
| CDR2 | KVSIRFS (Seq. ID No: 19) |
| FR3 | GVPDRFSGSGSGTDFTLNISRVEAEDLGIYYC (Seq. ID No: 20) |
| CDR3 | FQGSHVPYT (Seq. ID No: 21) |
| FR4 | FGGGTKLEIK (Seq. ID No. 22) |

TABLE 14-continued

| $V_L$ anti-KC-4 Amino Acid Sequences (kII-Jk2) |
|---|

TABLE 15

| Anti-KC-4 $V_H$ Amino Acid Sequences (IIID-D9-JH3) | |
|---|---|
| | MDFGLSLVFLVLILKGVQC (Seq. ID No: 23) |
| FR1 | EVQMVESGGGLVKPGGSLKLSCAASGFAFS (Seq. ID No: 24) |
| CDR1 | SYAMS (Seq. ID No: 25) |
| FR2 | WVRQSPEKRLEWVA (Seq. ID No: 26) |
| CDR2 | EISSGGNYAYYQDTVTG (Seq. ID No: 27) |
| FR3 | RFTISRDNAKNTLYLEMSSLRSEDTAMYYCAR (Seq. ID No: 28) |
| CDR3 | EGIPAWFAY (Seq. ID No: 29) |
| FR4 | WGQGTLVSVSA (Seq. ID No: 30) |

The sequences were interpreted as described by Kabat et al. (1991), supra. The residues that are underlined in the protein sequences correspond to PCR primer. The mature $V_L$ and $V_H$ chains begin at amino-acids D and E of framework 1 (FR1), respectively.

Framework and CDR protein segments were identified according to Kabat et al. (1991), supra. $V_L$ is a group II κ chain. Part of the CDR 3 and all of the framework 4 (FR4) are encoded by Jk2. $V_H$ belongs to group IIId. CDR 3 and FR 4 resulted from a genomic recombination involving minigenes D9 and JH3. There is an asparagine glycosylation site in the light chain in FR3. The site reads NIS (Asn IIe Ser).

Example 5

Comparison of cDNA-deduced Amino Acid Sequence with Directly Determined N-Terminal Fragment Sequence A comparsion between the cDNA-derived polypeptide sequence and the amino acid sequence determined directly on the purified anti-KC-4 monoclonal antibody was undertaken. The results are shown in Table 16 below.

TABLE 16

| Comparison of cDNA-deduced with Directly Determined N-Terminal Amino Acid Sequences | |
|---|---|
| FIRST BAND TOP | |
| $V_H$, cDNA-deduced | EVQMVESGGGLVKPGGSLKLS (Seq. ID No: 31) |
| $V_H$, Protein sequence | EVQMVESGGGLVKPGGXLKLS (Seq. ID No: 32) |

TABLE 16-continued

| Comparison of cDNA-deduced with Directly Determined N-Terminal Amino Acid Sequences | |
|---|---|
| SECOND BAND | |
| $V_L$, cDNA-deduced | DVLMTQTPLSLPVSLGDQASI (Seq. ID No: 33) |
| $V_L$, Protein sequence | DVLMTQTPLSLPVXXGDQASI (Seq. ID No: 34) |
| THIRD BAND | |
| $V_L$, cDNA-deduced | DVLMTQTPLSLPVSLGDQASI (Seq. ID No: 35) |
| $V_L$, Protein sequence | DVLMTQTPLSLPVSLGDQASI (Seq. ID No: 36) |

X uncertain or alternative calls.

A sample of anti-KC-4 chimeric antibody (approximately 190 μg) was reduced with 5% beta-mercaptoethanol (65° C. for 15 min.), separated on three lanes of a 10% SDS polyacrylamide gel, and electroblotted onto a ProBlott membrane (Applied Biosystems, Foster City, Calif.) in 90% 30 mM CAPS pH11, 10% methanol, for 1 hour at 25 V and at 4° C. The transferred protein species were stained with Commassie Brillant Blue. 3 bands were seen in each lane, of which 2 migrated as expected for a heavy and light chain. The third band migrated above the light chain. Amino acid sequencing was performed directly on the immobilized bands by the Biotechnology Instrumentation Facility, University of California, Riverside. The amino acid sequence given here is the sequencer's best guess.

The close match betweenther deduced amino acid sequence and the directly determined amino terminal sequence indicates that the cloned cDNAs encode the authentic anti-KC-4KC-4 $F_V$ region.

Example 6

Construction of Vectors Expressing Murine-Human Chimeric anti-KC-4 Antibody

The two expression vectors pAG4622 and pAH4604 described in Coloma et al. (Coloma, M. J., et al., "Novel Vectors for the Expression of Antibody Molecules Using Variable Regions Generated by PCR", J. Immunol. Methods 152:89–104 (1992)). These were kindly provided by S. L. Morrison (Dept. of Mircobiology and Molecular Genetics, UCLA), U.S. application Ser. No. 07/798,696; PCT/US91/10207. The construction and expression of chimeric genes were performed as described by Coloma et al., supra.

Oligonucleotides synthesized and used in a PCR to produce $V_H$ and $V_L$ fragments with the correct ends for insertion into the pAG4622 and pAH4604 expression vectors are shown in Table 17 below.

TABLE 17

| PCR Primers Sequences |
|---|
| JO20 - sense kappa leader<br>GGG GATATC CACC ATG AAG TTG CCT GTT AGG CTG TTG<br>(Seq. ID No: 9)<br>JO21 - antisense JK2<br>CCC GTCGACTTAC G TTT TAT TTC CAG CTT GGT CCC CCC T<br>(Seq. ID No: 10)<br>JO22 - sense $V_H$ leader<br>GGG GATATC CACC ATG GAC TTT GGG CTC AGC TTG GTT TT<br>(Seq. ID No: 11) |

TABLE 17-continued

| PCR Primers Sequences |
|---|
| JO24 - antisense JH3<br>CCC GCTAGC TGC AGA GAC AGA GAC CAG AGT CC<br>(Seq. ID No: 12) |

The original pCR1000 clones were the starting templates for the PCR. The new PCR products were cloned back into PCR1000 and their sequence confirmed. Correctly modified and amplified fragments were excised with either EcoR V and Sal I (for $V_L$) or with EcoR V and Nhe I (for $V_H$). These fragments were then ligated into the respective vectors, which had been cut open with the appropriate restriction enzymes. Both the vectors and the inserts were purified from an agarose gel prior to ligation, using the Bio101 GeneClean kit (glass beads) (La Jolla, Calif.).

Example 7

Expression of the anti-KC-4 Chimeric Antibody Gene

Once inserted in pAG4622 and pAG4604, the $V_H$ and $V_L$ encoding regions in the anti-KC-4 murine-human chimeric antibody constructs were sequenced once again to verify their accuracy. The transfection of the non-producer myelmoa cell line SP2/0-Ag14, (ATCC No. CRL 1581) and isolation of polypeptide was conducted as described in Coloma et al., (1992), supra

Example 8

Production of Chimeric Antibody in Transfected Hosts

After ten days, stable transfectant colonies were clearly established at a frequency of approximately 1/10,000. Transfected cells were cultured either in Dulbecco's modified Eagle's medium (DME): fetal bovine serum (FBS), 90:10 (v/v) or in a mixture of DME:RPMI:FBS, 45:45:10 (v/v/v) or RPMI:FBS, 90:10 (v/v). Penicillin and streptomycin were added to prevent bacterial growth. Histidinol was added to the medium, at 5 mM, in order to select for transfections. The colonies were transferred to normal medium (without histidinol) and the supernatants from stable transfectants were assayed for the presence of the murine-human chimeric anti-KC-4 antibody. This was done by capturing the secreted murine-human chimeric anti-KC-4 antibody with a plate-bound goat anti-human-κ antibody and developing with goat anti-human-γ antibody as described by Coloma et al. with the following modification. The secondary antibody utilized herein was radiolabeled with $^{124}$I.

Example 9

Confirmation of anti-KC-4 Murine Human Chimeric Antibody Expression

The supernatants were assayed for binding to human milk fat globule (HMFG) as described by Ceriani et al. (Ceriani R. L., et al., Diagnostic Ability of Different Human Milk Fat Globule Antigens in Breast Cancer", Breast Cancer Res. Treat. 15:161–174 (1990)). HMFG was bound to the microtiter plates as described previously (Certiani R. L., "Solid Phase Identification and Molecular Weight Determination of Cell Membrane Antigens with Monoclonal Antibodies", in: Monoclonal antibodies and functional cell lines. Progress and application, Bechtol, K. B., McKem, T. J., and Kennett, R., Eds., Plenum Press, New York, pp 398–402 (1984)). The bound anti-KC-4 chimeric antibody (to kappa chain polyclonal antibodies HMFG) was detected with either goat anti-human gamma chain or goat anti-human kappa chain polyclonal antibodies conjugated to $^{125}$I. Most colony supernatants were positive by both assays. The colonies that secreted the highest level of chimeric antibody in the supernatants, as determined by these assays, were subcloned.

Example 10

Western Blot

75 μl of the culture supernatant was added to 20 μl of 4× Laemmli buffer and 5 μl β-mercaptoethanol and the mixture was heated at 65° C. for 15 min., in order to reduce antibody disulfide bonds and, thus, separate heavy from light chains 20 μl of the treated sample was chromatographed in duplicate lanes on a 10% SDS polyacrylamide gel together with other antibodies that were treated similarly and that were loaded for comparison. Pre-stained size markers (BioRad, Richmond, Calif.) were also loaded. The chromatographed proteins were electroblotted onto a ProBlott membrane (Applied Biosystems, Foster City, Calif.) in 90% 30 mM CAPS pH11, 10% methanol, for 1 hour at 25 V and at 4° c. The membrane was cut into 2 parts containing identical antibody samples. The 2 membranes were immersed in 20% bovine calf serum in PBS and shaken slowly at room temperature for 1 hour 35 min. $^{125}$I-labeled goat anti-human κ chain antibody was added to one membrane and $^{125}$I labeled goat anti-human γ chain antibody to the other membrane. Antibodies were labeled at a specific activity of approximately 10 mCi/mg using the chloramine T method as described by Ceriani, R. L. and Blank, E. W. (1988), the labeled antibodies were diluted to 4,000 cpm/μl in RIA buffer.

After incubating 3 hours at room temperature the blots were washed twice in TBS for 10 min each time, once in TBST (50 mM TRIS pH7.5, 3 mM EDTA 25 mM NaCl) 10 min and once more in TBS (TBS with 0.05% Tween 20) for 10 min. The membranes were dried and exposed to Kodak XAR film.

Western blot analysis of culture supernatants revealed that three antibody chains were expressed that correspond to the three antibody chains seen in the original anti-KC-4 murine antibody. These were a heavy chain that stained with goat anti-human γ chain $^{125}$I-labeled antibody, and two light chains that stained with goat anti-human κ chain $^{125}$I-labeled antibody (Figure not shown).

The treatment of the original anti-KC-4 murine antibody with N-glycosidase F (Boehringer Mannheim GmbH Germany) following the recommendations of the manufacturer, produced a noticeable decrease in the intensity of the "top" chain and a concomitant increase in the intensity of the bottom light chain (FIG. not shown).

The explanation for the existence of an extra light chain is that this chain is glycosylated. Three lines of evidence substantiate this. First, the detection of an asparagine-linked glycosylation site in the amino acid sequence of the light chain. That is the triad NIS (Asn-Ile-Ser) in framework 3. Second, the decrease of the intensity in the putative glycosylated band after treatment with N-glycosidase F, while concomitantly the intensity of the non-glycosylated band was increased. Finally, 2 corresponding light chain bands are seen in the chimerci antibody version.

The extra light chain in the chimeric version cannot be a contaminant since it was specifically stained by a goat anti-human κ chain antibody. It can only be a product expressed by pAG4622. Thus both light chains must have the same $V_L$ amino acid sequence and the same human constant region. These observations show that approximately half of the light chains of both the anti-KC-4 murine and chimeric antibodies are glycosylated at the asparagine-linked glycosylation site.

Example 11

Tissue Binding Studies

The supernatants from stable transfectants were assayed for the presence of the anti-KC-4 murine-human chimeric antibody as described using the vectastain ABC method (Vector Labs, Burlingame, Calif.).

The chimeric antibody secreted in the supernatant bound both HMFG and BEM very strong. In addition, the supernatants containing anti-KC-4 murine-human chimeric antibody were used to stain human breast carcinoma tissue sections by using the immunoperoxidase immunohistochemical staining technique. The intensity of the staining was comparable to that obtained with the original murine monoclonal antibody.

The anti-KC-4 monoclonal antibody is known to bind the human milk fat globule and the breast epitherlial mucin. This binding specificity of the anti-KC-4 murine monoclonal antibody was maintained even after the recombinant procedure. The anti-KC-4 chimeric antibody bound very strongly to HMFG and BEM as determined by a radioassay (Ceriani, et al., Breast Cancer Res. Trent. 15:161 (1990)). In addition, the anti-KC-4 chimeric antibody bound several human beast tumors in histopathological sections in a manner comparable to the anti-KC-4 murine monoclonal antibody, detected by immunostaining using the vectastain ABC method (supra). This specificity of binding demonstrated the retained binding reactivity of the variable regions of anti-KC-4 murine antibody by the polypeptide of the invention when attached to the human $F_C$ fragment.

Example 12

Approach for Humanization of Antibodies

The present humanization approach is based on Padlan, E. A., "Choosing the Best Framework to Use in the Humanization of an Antibody by CDR-Grafting: Suggestions from 3-D Structural Data", Antibody Engineering 2nd. Annual Conf. San Diego, Calif. (Dec. 16–17, 1991).

The fine specificity may be preserved in a "humanized" antibody only if the CDR structures, their interaction with each other, and their interaction with the rest of the variable domains can be maintained. (Padlan, E. A. (1991) supra). This requires the preservation of residues of the FR amino acids which contact the CDRs, those which are involved in the $V_L$-$V_H$ contact, and those which are buried and could influence the overall domain structure and the structure of the combining site.

By examination of murine Fab structures, for which atomic coordinates are available, the FR amino acids that are probably "important" in maintaining the structure of the combining site may be determined (Padlan, E. A., 8th International Congress of Immunol., Budapest, Hungary, Abstracts p. 19 (August 2–28, 1992)).

The specificity of an antibody depends on the CDR structures and sometimes, on some of its neighboring residues as well. These CDR structures, in turn depend on contacts with framework amino acids and on the interaction of the $V_L$ and $V_H$ domains. Thus, to ensure the retention of binding affinity, not only the CDR residues must be preserved, but also those FR residues that contact either the CDRs or their opposite domains, as well as all buried residues, which give shape to the variable domains. The buried amino acids are placed in exactly the same positions in human and in murine frameworks (Padlan, E. A., "A Possible Procedure for Reducing the Immunogenicity of Antibody Variable Domains While Preserving Their Ligand-Binding Properties", Molecular Immunology 28:489–498 (1991)).

This approach was applied to design humanized analogues of the variable regions of the murine antibodies of the invention. The humanization or design of the exemplary analogue peptide provided herein was undertaken as follows. The identification of the residues, which are most probably "important" in preserving the combining site structure, permits the selection of the best human FR sequences to use in the "humanization" of each chimeric antibody of known structure or analogue peptides of the invention. The results of the analysis can be used also to predict which FR amino acids should probably be retained in those cases where no three-dimensional structural data are available.

The present procedure was designed to reduce the immunogenicity of the xenogeneic antibodies by preparation of their chimeric derivatives or fragments thereof while preserving their antigen-binding properties. In general, the antigen binding properties of an antibody are primarily determined by its CDRs. The CDRs of the murine antibody were therefore, completely retained. In addition, the FR amino acids in the murine antibody, that are judged as probably important in maintaining the combining site structure, were also retained in the humanized molecule. The remainder FR amino acids were changed to match those of the chosen human FR.

Example 13

Choice of Murine Model of Known Structure for Humanization of anti-KC-4 Antibody The classification of the $V_H$ and $V_L$ domains of an antibody such as the anti-KC-4 antibody was done according to Kabat et al. (Kabat, E. A., et al., "Sequence of Proteins of Immunological Interest" NIH (1991). The KC-4G3 kappa chain $V_L$ domain belongs to group II and the $V_H$ domain belongs to group IIId. A murine antibody was then found, whose structure had been determined, and whose variable regions belong to the same classes. The anti-myobemerythrin peptide antibody B1312 fits these requirements since, like the anti-KC-4 murine antibody, it has $V_L$ and $V_H$ domains belonging to groups II and IIId (Stanfield, R. L. et al., "Crystal Structures of an Antibody to a Peptide and its complex with Peptide Antigen at 2.8 Å", Science 248:712–719 (1990)). Thus, the three-dimensional structures of antibodies the anti-KC-4 and B1312 antibodies should be similar, and the humanization of the anti-KC-4 antibody may be modeled after B1312.

Example 14

Choice of Target Human Framework for Humanization of Chimeric anti-KC-4 Antibody The choice of the target human framework was based strictly on the similarity at the residues that were judged to be structurally important according to the B1312 model. That is, only amino acids that could be involved in contacts with CDRs of the opposite chain, or amino acids whose side-chains were predicted to be inwardly pointed. The positions of these amino acids are shown in Table 18 below.

TABLE 18

| Important Amino Acid Positions for anti-KC-4 Antibody |
|---|
| Light Chain Variable Region Framework |
| 2, 3, 4, 6, 7, 11, 13, 19, 21, 22, 23, 35, 36, 37, 38, 43, 44, 46, 47, 48, 49, 58, 60, 61, 62, 69, 71, 73, 75, 78, 82, 85, 86, 87, 88, 98, 102, 104 and 106. |
| Heavy Chain Variable Region Framework |
| 2, 4, 6, 12, [001b]18, 20, 22, 24, 27, 28, 29, 36, 37, 38, 39, 43, 45, 46, 47, 48, 49, 66, 67, 69, 71, 78, 80, 82, 82c, 86, 88, 90, 91, 92, 93, 94, 103, 107, 109 and 111. |

The numbering system is conventionally accepted (Kabat, et al. (1991), supra) and is shown in Tables 10 and 11 above. In this case, the consensus sequences of all human $F_V$ regions were selected as the target human framework to minimize the immunogenicity of the product.

First, the sequences of the murine variable chains were aligned with consensus sequences from all known variable region classes (Herron, J. N., (1989), supra) and the number of differences in the amino-acids that must be retained from the murine were scored. The positions of these amino acids were obtained from those of the B1312 murine monoclonal antibody, which was chosen to model the humanization of the anti-KC-4 antibody.

Based on the these scores, the consensus sequences human frameworks belonging to groups $V_\kappa$II and $V_H$III were chosen to receive the anti-KC-4 murine antibody CDRs plus other important amino acids.

Example 15

Identification of Murine-Human anti-KC-4 Antibody Differences

The original murine sequences (anti-KC-4 $V_\kappa$and $V_H$) were aligned with their closest human (Human KII or HIII) relatives (see, Example 14 above), and the differences in the FR amino acids were noted. In the present example, it was intended to be substituted as many amino acids as possible in going from the murine to the humanized variable consensus sequences, leaving the important amino acids intact as described in Examples 14 and 16. The amino acids chosen to be preserved were subset,of those listed above. Those were selected by analogy to the B1312 sequence. The single exception was the glycine (100) residue of the original framework of the variable region of the murine kappa chain, which was retained despite not being encompassed in Table 18 above since it was thought that it might contact the variable domain of the heavy chain. Such contacts were observed in at least three FAB that lack a gly at this position.

Example 16

Identification of Important Murine anti-KC-4 Antibody Amino Acids

The "important" murine amino acids were chosen for preservation based on the contacts of a particular amino acid with the CDRs, and with the opposite chains and/or whether their side chains are pointing inwardly or outwardly. The positions of these "important" amino acids were determined based on the examination of the known structures of other antibodies.

Most of the "important" amino acids were selected on the basis of the structure of antibody B1312 and according to Tables 2, 3, 4, 5, 6, 8 and 9 above.

The final selection of amino acid positions for actual mutation was attained by comparing the position of all amino acids that are candidates for mutation with those that are "important" and should be preserved. Any "important" amino acid position was eliminated from the list of candidates. Table 19 below shows the amino acids that were selected for change in the murine sequence to attain the humanized sequence in the present exemplary analogue.

TABLE 19

Anti-KC-4 Murine Antibody Variable Region Amino Acids Selected for Mutation

| Position | KC-4G3 Murine Identity → | Consensus Human Identity |
|---|---|---|
| Light Chain | Variable Region | T |
| 14 | S | T |
| 15 | L | P |
| 17 | D | E |
| 18 | Q | P |
| 45 | K | Q |
| 74 | N | K |
| 83 | L | V |
| Heavy Chain | Variable Region | |
| 13 | K | Q |
| 19 | K | R |
| 40 | S | A |
| 42 | E | G |
| 44 | R | G |
| 74 | A | S |
| 61 | E | Q |
| 82a | S | N |
| 84 | S | A |
| 89 | M | V |
| 110 | S | T |
| 113 | A | S |

The change N→K at position 74 in the variable light chain knowingly eliminated an N-linked glycosylation site, which was present in the original murine monolonal antibody.

Example 17

Introduction of Changes in Amino Acid Sequence for Humanization of anti-KC-4 Antibody The introduction of the changes in the amino acid sequence was conducted as follows. The DNA encoding each humanized variable region was synthesized in a single polymerase chain reaction (PCR) using overlapping oligonucleotides in accordance with the method described by Ye et al. (Ye, Q-Z, Johnson, L. L., and Baragi, V., "Gene Synthesis and Expression in E. coli for PUMP, a Human Matrix Metalloproteinase", BBRC 186(1):143–149 (1992)). The sequences of the oligonuclcotides are shown in Table 20 below.

TABLE 20

| Primers for Humanization of anti-KC-4 Murine Antibody Variable Regions | |
|---|---|
| JA59 | CCCGGATCC TTTAAAAGGT GTCCAGTGTG AAGTGCAGAT GGTGGAG TCT G (SEQ. ID No.: 37) |
| J060 | GAATTCGGGGC TAGCACTAGA GACAGTGACC AGAGTCCCTT GGCCC CAG (SEQ. ID No.: 38) |
| J061 | AGTGCAGATG GTGGAGTCTG GGGGAGGCTT AGTGCAGCCT GGAGGG TCCC TGAGACTCTC CTGTGCAGCC TCTGGATTCG CTTTCAGTAG CTATGCCATG T (SEQ. ID No.: 39) |
| J062 | CTTGATAGTA GGCGTAATTA CCACCACTAC TAATTTCTGC GACCCA CTCC AGCCCCTTCC CTGGAGCCTG GCGAACCCAA GACATGGCAT AGCTACTGAA A (SEQ. ID. No.: 40) |
| J063 | TAATTACGCC TACTATCAAG ACACTGTGAC GGGCCGATTC ACCATC TCCA GAGACAATTC CAAGAACACC CTGTACCTGC AAATGAACAG TCTGAGGGCT G (SEQ. ID. No.: 41) |
| J064 | CCAGAGTCCC TTGGCCCCAG TAAGCAAACC AGGCCGGGAT ACCGTA GTCC TCCCTTGCAC AGTAATACAC GGCCGTGTCC TCAGCCCTCA GACTGTTCAT T (SEQ. ID. No.: 42) |
| J073 | GGGAAGCTTG ATATCCACCA TGAAGTTGCC TGTTAGGCTG TTGGTG CTGA TGTTCTGGAT TCCTGC (SEQ. ID. No.: 43) |
| J074 | AAAGATTCG TCGACTTACG TTTTATTTCC AGCTTGGTCC CCCCTCC GAA CGTGTACGGA ACATGT (SEQ. ID. No.: 44) |
| J075 | CTGATGTTCT GGATTCCTGC TTCCAGCAGT GATGTTTTGA TGACCC AAAC TCCTCTCTCC CTGCCTGTCA CTCCAGGAGA GCCAGCCTCC ATCTCTTGCA (SEQ. ID. No.: 45) |
| J076 | CTGTGGAGAC TGGCCTGGTT TCTGCAGGTA CCATTCTAAA TAGGTG TTTC CATTACTATG TACAATGCTC TGACTAGATC TGCAAGAGAT GGAGGCTGGC (SEQ. ID. No.: 46) |
| J078 | CGAACGTGTA CGGAACATGT GAACCTTGAA AGCAGTAATA AATTCC CACA TCCTCAGCCT CCACTCTGCT GATCTTGAGT GTGAAATCTG TCCCTGATCC (SEQ. ID. No.: 47) |

Example 18

Synthesis of Primers for Humanization of anti-KC-4 Antibody

All primers were synthesized on a PCR-Mate EP DNA synthesizer model 391 (Applied Biosystems, Foster City, Calif.) using 40 nmole columns, cycle 1:63, with Trityl off. None were purified before use. Their sequences are shown in Table 20 above.

Example 19

Synthesis of anti-KC-4 Humanized Heavy Chains Variable Regions

A mixture of PCR primers was made, where each primer was present at a concentration of 10 prmole/μd in water.

Four 101 'mer oligonucleotides (JO61, JO62, JO63 and JO64), one 50'mer (JO59) and one 49'mer (JO60), were used for synthesis of the humanized variable heavy chain. The oligonucleotides concentration were estimated using the formula $$c=[(A_{2\infty})/30]\mu g/\mu l$$

The PCR amplification conditions were as follows. All reagents as well as the GeneAmp PCR system 9600 were purchased from Perkin Elmer Cetus. Optimal PCR conditions were determined empirically for each pair of mutagenic primers. A matrix of conditions varying the concentration of $MgCl_2$, mutagenic primer, and template plasmid DNA were set up as follows. However, the annealing and extension temperatures during PCR may be varied.

| | |
|---|---|
| 2 μM primer JO59 | 150 nM each of primers JO61, 62, 63 and 64. |
| 2 μM primer JO60 | 200 μM each of dGTP, dATP, TTP, and dCTP. |
| 10 mM KCl | 20 mM Tris-HCl pH 8.8 |
| 10 mM $(NH_4)_2SO_4$ | 2 units per 100 μl reaction Vent DNA |
| 0.1% Triton X-100 | polymerase (New England Biolabs) |
| | 6 mM $MgSO_4$ |

Example 20

Hot Start PCR for Humanization of anti-KC-4 Antibody

All the components of the PCR mixture, with the exception of Vent DNA polymerase, were mixed. The mixture was then dispensed in 19 μl aliquots in 5 PCR tubes. The reason for performing five independent reactions was to decrease the odds that unwanted mutations be isolated as a result of nucleotide misincorporation during PCR. The tubes were heated to 95° C. for 5 minutes and then cooled to 72° C. While at that temperature 1 μl of an appropriate Vent DNA polymerase dilution in 1×buffer was added to the reaction mixture (hot start). The temperature cycling then proceeds as follows.

[(96° C., 6 sec) (55° C., 10 sec) (72° C., 30 sec)] 3 cycles

[(96° C., 5 sec) (60° C., 10 sec) (72° C., 30 sec)] 29 cycles

72° C., 10 min

Example 21

Extra Final Extension for Humanized anti-KC-4 Antibody $V_H$ DNA

After cycling, one extra final extension reaction was carried out Extra deoxyribonucleotide triphosphates (to 125 μM) and 1 unit of Vent DNA polymerase were added, and the mixture was heated to 72° C. for 10 minutes.

The resulting synthetic DNA fragment was digested with DraI and NbeI and inserted into the same restriction sites an intermediate plasmid construct encoding the corresponding murine heavy chain variable region as described in examples 23 to 25.

Example 22

Synthesis of anti-KC-4 Humanized Light Chain Variable Regions

The light chain variable region ($V_L$) genes were synthesized in a similar way as described in Examples 22 to 24 above for the heavy chain signal peptide variable regions. In this case, however, the complete signal peptide and the $V_L$ encoding DNA were contained between EroRV and SalI. This DNA was inserted (ligated) into pBluescriptIIKs$^+$ (Stratagene) as described in examples 23 and 25.

Example 23

Purification of Humanized anti-KC-4 PCR Products

The PCR products were then separated on a 0.8% agarose gel in 1XTAE buffer and 0.5 μg/ml ethidium bromide. The correct DNA bands were visualized with UV light (366 nm), excised from the gels and extracted with the GeneClean kit (Bio 101, La Jolla, Calif.).

Example 24

Ligation of Humanized anti-KC-4 DNA to Plasmids (Reclosure of Plasmid)

The ligation mixtures consisted of 5 μl extracted DNA, 2 μl 10× ligation buffer (NEB) 1 μl T4 DNA polymerase (NEB), 12 μl water. The amount of plasmid DNA may be varied depending of the intensity of the band extracted from the Gel. Ligations were carried out at room temperature for 2 hrs., or alteratively at 14° C. overnight.

Example 25

Transformation and Sequencing of Humanized anti-KC-4 DNA

The reclosed plasmids were then transformed into E. coli utilizing Inv alpha F' competent cells purchased from Invitrogen Corporation, San Diego Calif. Plasmid DNA was then prepared from a few transformants and sequenced to verify that mutagenesis was successful.

Example 26

Hybrid Plasmid Preparation and Sequencing

Plasmid DNA was then prepared and sequenced to verify that the gene synthesis was successful. The anti-KC-4 humanized DNA sequences for the $V_H$ and $V_L$ segments are shown in Tables 21 and 22 below.

TABLE 21

| Humanized anti-KC-4 Antibody $V_L$ DNA sequences |
|---|
| anti-KC-4 $V_L$ FR-HZ |
| ATG AAG TTG CCT GTT AGG CTG TTG GTG CTG ATG TTC TGG ATT CCT GCT TCC AGC AGT GAT GTT TTG ATG ACC CAA ACT CCT CTC TCC CTG CCT GTC ACT CCA GGA GAG CCA GCC TCC ATC TCT TGC AGA TCT AGT CAG AGC ATT GTA CAT AGT AAT GGA AAC ACC TAT TTA GAA TGG TAC CTG CAG AAA CCA GGC CAG TCT CCA CAG CTC CTG ATC TAC AAA GTT TCC ATC CGA TTT TCT GGG GTC CCA GAC AGG TTC AGT GGC AGT GGA TCA GGG ACA GAT TTC ACA CTC AAG ATC AGC AGA GTG GAG GCT GAG GAT GTG GGA ATT TAT TAC TGC TTT CAA GGT TCA CAT GTT CCG TAC ACG TTC GGA GGG GGG ACC AAG CTG GAA ATA AAA C (SEQ. ID. NO.: 48) |

TABLE 22

| Humanized anti-KC-4 Antibody $V_H$ DNA Sequences |
|---|
| anti-KC-4 $V_H$ FR-HZ |
| ATG GAC TTT GGG CTC AGC TTG GTT TTC CTT GTC CTT ATT TTA AAA GGT GTC CAG TGT GAA GTG CAG ATG GTG GAG TCT GGG GGA GGC TTA GTG CAG CCT GGA GGG TCC CTG AGA CTC TCC TGT GCA GCC TCT GGA TTC GCT TTC AGT AGC TAT GCC ATG TCT TGG GTT CGC CAG GCT CCA GGG AAG GGG CTG GAG TGG GTC GCA GAA ATT AGT AGT GGT GGT AAT TAC GCC TAC TAT CAA GAC ACT GTG ACG GGC CGA TTC ACC ATC TCC AGA GAC AAT TCC AAG AAC ACC CTG TAC CTG CAA ATG AAC AGT CTG AGG GCT GAG GAC ACG GCC GTG TAT TAC TGT GCA AGG GAG GAC TAC GGT ATC CCG GCC TGG TTT GCT TAC TGG GGC CAA GGG ACT CTG GTC ACT GTC TCT AGT (SEQ. ID. No.: 49) |

Example 27

Expression of anti-KC-4 Humanized Antibody

Two expression vectors pAG4622 and pAH4604 (Coloma, M. J., et al. (1992), supra) were used that were developed and provided by S. L. Morrison (Dept. of Microbiology and Molecular Genetics, UCLA). Any cDNA encoding a signal peptide and either the variable heavy chain or the variable light chain can, in principle, be inserted into these vectors resulting in a construction that encodes an IgG1, K, antibody with human constant regions. Synthetic DNA fragments were excised from their intermediate plasmids (see examples 21 and 22) with either EcoRV and Sal to be inserted into pAG4622(light chain vector), or with EcoRV and NbEl to be inserted into pAH4640 (heavy chain vector). The restriction and ligation reactions necessary to accomplish these operations were performed under the conditions stipulated by the enzyme manufacturers (New England Biolabs, Beverly, Mass.). Both the vectors and the inserts were purified from an agarose gel prior to ligation, using the Bio101 (La Jolla, Calif.) GeneClean kit (glass beads). The $V_H$ and $V_L$ regions in the final constructions were sequenced once again to verify that they were correct. The non-producer mycloma cell line SP2/0-Ag14, ATCC: CRL 1581, (Shulman M., et al. (1978), supra) was transfected with both plasmid constructions, and antibody producers were isolated following the recommendations outlined in Coloma et al. (Coloma, M. J. et al. (1992), supra) except that selection was done only for the uptake of hisD (by adding 5 mM histidinol to the medium and readjusting the pH to 7.4 with NaOH). Usually after ten days, stable transfectant colonies were established at a frequency of approximately $10^{-3}$ to $10^{-4}$. Colonies were then transferred to normal medium (without histidinol). The culture media were either Dulbeco's modified Eagle's medium (DME): fetal bovine serum (FBS), 90:10, v/v, or a mixture of DME:RPMI:FBS, 45:45:10, v/v/v. Penicillin and streptomycin were added to prevent bacterial growth.

The supernatants from stable transfectants were assayed for the presence of the antibodies. This was done by capturing the secreted chimeric antibody with a plate-bound goat anti-human-kappa chain antibody and developing with goat anti-human-gamma chain antibody, essentially as described previously (Coloma, M. J., (1992), supra) except that the secondary antibody was radiolabeled with $^{125}$I. The supernatants were also assayed for binding to human milk fat globule (HMFG) as described previously (Ceriani R. L., et al., "Diagnostic Ability of Different Human Milk Fat Globule Antigens in Breast Cancer", Breast Cancer Res. Treat. 15:161–174 (1990)). HMFG is bound to the microtiter plates as described previously (Ceriani, R. I. (1984), supra). Usually most colony supernatants were positive by both assays.

Colonies that secrete the highest level of antibody in the supernatants, as determined by these assays, were subcloned and subsequently adapted to serum-free medium for the purification of antibody. Serum free medium contains HL-1 supplement as directed by the manufacturer (Ventrex Labs, Portand, Me.).

Example 28

Half Humanized-Half Chimeric anti-KC-4 Antibody

An anti-KC-4 humanized light chain was paired with an anti-KC-4 non-humanized chimeric heavy chain by co-transfection of SP2/0Ag14 mycloma cells with hybrid plasmids carrying the respective DNA sequences and those of a human $F_C$. The resulting antibody was named "HuKC4V1" (ATCC No. HB 11454).

In addition, an anti-KC-4 humanized heavy chain was paired with an anti-KC-4 non-humanized chimeric light chain as described in Example 27 above. The resulting antibody was named "HuKC4V3" (ATCC No. HB 11456).

Example 29

Fully Humanized anti-KC-4 Antibody

An anti-KC-4 fully humanized antibody was prepared by pairing fully humanized anti-KC-4 light and heavy chains by co-transfection as described in Example 27 above. The fully humanized versions is named "HuKC4V2" (ATCC No. HB 11455).

Example 30

Determination of Affinity Constants for Fully Humanized anti-KC-4 Antibody

The secreted fully humanized antibody (HuKC4V2) was purified from culture supernatants using a Sepharose 4B -protein A column (Bio-Rad, Richmond, Calif.) as described by Ey et al. (Ey, P. L, et al. (1978), supra). Microtiter plates (Dynatech, Chantilly, Va.) were prepared as described by Ceriani et al. (Ceriani R. L., et al. (1992), supra) using successive layers of methylated BSA, glutaraldehyde, anti-β-galactosidase and the bacterial fusion protein 11-2 (a hybrid of β-galactosidase and human mammary mucin). Each well contained 388 mg of the 11-2 fusion protein. To each well were added 25 μl $^{125}$I-KC-4 in RIA buffer (10% bovine calf serum, 0.3% triton X-100, 0.05% sodium azide pH 7.4, in phosphate buffer saline) and compete with 25 μl of either unlabeled murine or chimeric antibody in RIA buffer at the final concentrations of 130 pM, 850 pM, 1.3 nM, 4 nM, and 13 nM). Iodinations were performed with $^{125}$I (17 Ci/mg, Nordion International). 50 μg anti-KC-4 monoclonal antibody (Coulter, Hialeah, Fla.) were labeled at a specific activity of 9.56 mCi/mg using the chloramine T method as described previously by Ceriani et al. (Ceriani R. L., et al., (198), supra).

The antibody-antigen affinity constants were determined by taking the reciprocal of the concentration of competing unlabeled monoclonal antibody that produced 50% binding as described by Sheldon et al. (Sheldon K., et al. (1987), supra).The protocol used to determine affinity constants was as described above except that in each case, an unlabeled antibody competed for binding to the antigen against the same radiolabeled antibody. The fully humanized antibody was shown to compete as well as anti-KC-4 murine antibody against radiolabeled anti-KC-4 murine antibody for binding to the KC-4G3 antigen.

Polyacrylamide gel electrophoresis was performed to insure that the antibody chains migrated as expected. The affinity binding constants of the murine, chimeric, half humanized and humanized antibodies were determined in independent competition assays. The binding affinities of the murine and anti-KC-4 and HuKC4V2 antibodies for the KC-4G3 antigen were determined to be similar.

Example 31

Histochemical Specificity of Fully Humanized Antibody

Immunohistochemical staining using the immunoperoxidase technique of consecutive human breast carcinoma tissue sections was used as a test to verify that the analogue antibodies retain the affinity for the KC-4G3 carcinoma antigen of the murine antibody. Breast carcinoma tissue sections were stained with the supernatant of the KC-4 murine and fully humanized transfected cells using the Vectastain ABC method (Vector Labs, Burlingame, Calif.). Both antibodies showed strong staining patterns.

The following Table 23 shows the results of the immunoperoxidase staining of five human breast carcinomas with either the standard anti-KC-4G3 murine or the fully humanized antibodies. Both stained the same tissues at a comparative level.

TABLE 23

Immunoperoxidase Staining of Human Breast Carcinoma Tissue Sections with Murine and Fully Humanized anti-KC-4 Antibodies

| Breast Tumor | Murine Antibody | Fully Humanized Antibody |
|---|---|---|
| 1 | ++ | ++ |
| 2 | +++ | +++ |
| 3 | – | – |

TABLE 23-continued

Immunoperoxidase Staining of Human Breast Carcinoma Tissue Sections with Murine and Fully Humanized anti-KC-4 Antibodies

| Breast Tumor | Murine Antibody | Fully Humanized Antibody |
|---|---|---|
| 4 | ++ | ++ |
| 5 | +++ | +++ |

Example 32

Binding to HMFG of Half Humanized and Fully Humanized anti-KC-4 Antibodies

Tissue culture supernatants from transfections of all three anti-KC-4 variants of the humanized antibody were shown to bind the human milk fat globule (HMFG) as determined by radio-immunodetections.

Example 33

Half Humanized and Fully Humanized anti-KC-4 Antibodies Bind to Goat anti-Human κ or γ Antibodies Tissue culture supernatants from transfections of all three variants of the anti-KC-4 humanized antibody were shown to bind in sandwich radioimmunodetections to both goat anti-human kappa chain antibody bound to microtiterplate wells (750 ng/well), and to radio-iodinated $^{125}$I-labeled goat anti-human gamma chain antibodies.

The results of these sandwich assays demonstrate that both chains of the humanized antibodies indeed possess human kappa and gamma constant regions.

Example 34

Deduced Amino Acid Sequence of Humanized anti-KC-4 Variable Light and Heavy Chains The amino acid sequences of the light and heavy chains of the analogue humanized antibody are shown in Tables 24 and 25 below. The actual amino acid sequences may be varied either to increase affinity for the antigen or to decrease immunogenicity in humans. Numerous variants of this sequence may be engineered in accordance with the invention.

TABLE 24

Humanized anti-KC-4 Antibody $V_L$ Analogue Sequence anti-KC-4 $V_L$ FR-HZ

| | | | | |
|---|---|---|---|---|
| MKLPVRLLVL | MFWIPASSSD | VLMTQTPLSL | PVTPGEPASI | SCRSSQSIVH |
| SNGNTYLEWY | LQKPGQSPQL | LIYKVSIRFS | GVPDRFSGSG | SGTDFTLKIS |
| RVEAEDVGIY | YCFQGSHVPY | TFGGGTKLEI | K | (Seq. ID No: 50) |

TABLE 25

Humanized anti-KC-4 Antibody $V_H$ Analogue sequence anti-KC-4 $V_H$ FR-HZ

| | | | | |
|---|---|---|---|---|
| MDFGLSLVFL | VLILKGVQCE | VQMVESGGGL | VQPGGSLRLS | CAASGFAFSS |
| YAMSWVRQAP | GKGLEWVAEI | SSGGNYAYYQ | DTVTGRFTIS | RDNSKNTLYL |
| QMNSLRAEDT | AVYYCAREDY | GIPAWFAYWG | QGTLVTVSS | (Seq. ID No: 51) |

Example 35

[Hybridoma] Cell Deposits

The following cell lines were deposited as present examples of the best mode of the invention. The [hybridoma] cell line expressing the anti-KC4 murine-human chimeric antibody was deposited with the ATCC on Nov. 13, 1992 under the Budapest Treaty, and has been assigned Accession No. HB 11201 (Chimeric anti-KC-4 1E8). The [hybridoma] cell line*s* expressing the anti-KC-4 fully humanized antibody (huKC4V2), and the half humanized anti-KC-4 antibodies (huKC4V1 and huKC4V3) were deposited with the ATCC on Sep. 23, 1993 and have been assigned Accession Nos. HB 11455 (Humanized HuKC-4 V2), HB 11454 (Half Humanized HuKC4V1), and HB 11456 (Half Humanized HuKC4V3).

The invention now being fully described, it will be apparent to one of ordinary skill in the art that many changes and modifications can be made thereto without departing from the spirit or scope of the invention as set forth herein.

SEQUENCE LISTING (1) GENERAL INFORMATION:

(iii) NUMBER OF SEQUENCES: 51

(2) INFORMATION FOR SEQ ID NO: 1:

(i) SEQUENCE CHARACTERISTICS:
(A) LENGTH: 40 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 1:

ACTAGTCGAC ATGAAGTTGC CTGTTAGGCT GTTGGTGCTG 40

(2) INFORMATION FOR SEQ ID NO: 2:

(i) SEQUENCE CHARACTERISTICS:
(A) LENGTH: 39 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 2:

ACTAGTCGAC ATGGAGWCAG ACACACTCCT GYTATGGGT 39

(2) INFORMATION FOR SEQ ID NO: 3:

(i) SEQUENCE CHARACTERISTICS:
(A) LENGTH: 40 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 3:

ACTAGTCGAC ATGGATTTWC AGGTGCAGAT TWTCAGCTTC 40

(2) INFORMATION FOR SEQ ID NO: 4:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 4:

CCCAAGCTTA CTGGATGGTG GGAAGATGGA 30

(2) INFORMATION FOR SEQ ID NO: 5:

(i) SEQUENCE CHARACTERISTICS:
(A) LENGTH: 35 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 5:

-continued

ACTAGTCGAC ATGRACTTTG GGYTCAGCTT GRTTT 35

(2) INFORMATION FOR SEQ ID NO: 6:

(i) SEQUENCE CHARACTERISTICS:
(A) LENGTH: 33 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 6:

ACTAGTCGAC ATGAGAGTGC TGATTCTTTT GTG 33

(2) INFORMATION FOR SEQ ID NO: 7:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 7:

ACTAGTCGAC ATGGATTTTG GGCTGATTTT TTTTATTG 38

(2) INFORMATION FOR SEQ ID NO: 8:

(i) SEQUENCE CHARACTERISTICS:
(A) LENGTH: 35 base pairs
(B) TYPE: nucleic acid
(C) STRANDEDNESS: double
(D) TOPOLOGY: linear (ii) MOLECULE TYPE: cDNA
(B) MAP POSITION: Nucleotide position No. 30

(ix) FEATURE:
(A) NAME/KEY: Modified base; N = inosine (xi) SEQUENCE DESCRIPTION: SEQ ID NO: 8:

CCCAAGCTTC CAGGGRCCAR KGGATARACN GRTGG 35

(2) INFORMATION FOR SEQ ID NO: 9:

(i) SEQUENCE CHARACTERISTICS:
(A) LENGTH: 37 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 9:

GGGGATATCC ACCATGAAGT TGCCTGTTAG GCTGTTG 37

(2) INFORMATION FOR SEQ ID NO: 10:

(i) SEQUENCE CHARACTERISTICS:
(A) LENGTH: 39 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 10:

-continued

CCCGTCGACT TACGTTTTAT TTCCAGCTTG GTCCCCCCT 39

(2) INFORMATION FOR SEQ ID NO: 11:

(i) SEQUENCE CHARACTERISTICS:
(A) LENGTH: 39 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 11:

GGGGATATCC ACCATGGACT TTGGGCTCAG CTTGGTTTT 39

(2) INFORMATION FOR SEQ ID NO: 12:

(i) SEQUENCE CHARACTERISTICS:
(A) LENGTH: 32 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 12:

CCCGCTAGCT GCAGAGACAG AGACCAGAGT CC 32

(2) INFORMATION FOR SEQ ID NO: 13:

(i) SEQUENCE CHARACTERISTICS:
(A) LENGTH: 394 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 13:

ATGAAGTTGC CTGTTAGGCT GTTGGTGCTG ATGTTCTGGA TTCCTGCTTC CAGCAGTGAT 60

GTTTTGATGA CCCAAACTCC TCTCTCCCTG CCTGTCAGTC TTGGAGATCA AGCCTCCATC 120

TCTTGCAGAT CTAGTCAGAG CATTGTACAT AGTAATGGAA ACACCTATTT AGAATGGTAC 180

CTGCAGAAAC CAGGCCAGTC TCCAAAGCTC CTGATCTACA AAGTTTCCAT CCGATTTTCT 240

GGGGTCCCAG ACAGGTTCAG TGGCAGTGGA TCAGGGACAG ATTTCACACT CAATATCAGC 300

AGAGTGGAGG CTGAGGATCT GGGAATTTAT TACTGCTTTC AAGGTTCACA TGTTCCGTAC 360

ACGTTCGGAG GGGGGACCAA GCTGGAAATA AAAC 394

(2) INFORMATION FOR SEQ ID NO: 14:

(i) SEQUENCE CHARACTERISTICS:
(A) LENGTH: 394 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 14:

ATGGACTTTG GGCTCAGCTT GGTTTTCCTT GTCCTTATTT TAAAAGGTGT CCAGTGTGAA 60

GTGCAGATGG TGGAGTCTGG GGGAGTGAAG CCTGGAGGGT CCCTGAAACT CTCCTGTGCA 120

GCCTCTGGAT TCGCTTTCAG TAGCTATGCC ATGTCTTGGG TTCGCCAGGA GAAGAGGCTG 180

-continued

```
GAGTGGGTCG CAGAAATTAG TAGTGGTGGT AATTACGCCT ACTATCAAGA CACTGTGACG    240

GGCCGATTCA CCAGAGACAA TGCCAAGAAC ACCCTGTACC TGGAAATGAG CAGTCTGAGG    300

TCTGAGGACA CGGCCATGTA TTACTGTGCA AGGGAGGGTA TCCCGGCCTG GTTTGCTTAC    360

TGGGGCCAAG GGACTCTGGT CTCTGTCTCT GCAG                                394
```

(2) INFORMATION FOR SEQ ID NO: 15:

(i) SEQUENCE CHARACTERISTICS:
(A) LENGTH: 19 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 15:

```
Met Lys Leu Pro Val Arg Leu Leu Val Leu Met Phe Trp Ile Pro Ala
1               5                   10                  15

Ser Ser Ser
```

(2) INFORMATION FOR SEQ ID NO: 16:

(i) SEQUENCE CHARACTERISTICS:
(A) LENGTH: 23 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 16:

```
Asp Val Leu Met Thr Gln Thr Pro Leu Ser Leu Pro Val Ser Leu Gly
1               5                   10                  15

Asp Gln Ala Ser Ile Ser Cys
            20
```

(2) INFORMATION FOR SEQ ID NO: 17:

(i) SEQUENCE CHARACTERISTICS:
(A) LENGTH: 16 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 17:

```
Arg Ser Ser Gln Ser Ile Val His Ser Asn Gly Asn Thr Tyr Leu Glu
1               5                   10                  15
```

(2) INFORMATION FOR SEQ ID NO: 18:

(i) SEQUENCE CHARACTERISTICS:
(A) LENGTH: 15 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 18:

```
Trp Tyr Leu Gln Lys Pro Gly Gln Ser Pro Lys Leu Leu Ile Tyr
1               5                   10                  15
```

(2) INFORMATION FOR SEQ ID NO: 19:

(i) SEQUENCE CHARACTERISTICS:
(A) LENGTH: 7 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 19:

```
Lys Val Ser Ile Arg Phe Ser
1               5
```

(2) INFORMATION FOR SEQ ID NO: 20:

(i) SEQUENCE CHARACTERISTICS:
(A) LENGTH: 32 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 20:

```
Gly Val Pro Asp Arg Phe Ser Gly Ser Gly Ser Gly Thr Asp Phe Thr
1               5                   10                  15

Leu Asn Ile Ser Arg Val Glu Ala Glu Asp Leu Gly Ile Tyr Tyr Cys
            20                  25                  30
```

(2) INFORMATION FOR SEQ ID NO: 21:

(i) SEQUENCE CHARACTERISTICS:
(A) LENGTH: 9 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 21:

```
Phe Gln Gly Ser His Val Pro Tyr Thr
1               5
```

(2) INFORMATION FOR SEQ ID NO: 22:

(i) SEQUENCE CHARACTERISTICS:
(A) LENGTH: 10 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 22:

```
Phe Gly Gly Gly Thr Lys Leu Glu Ile Lys
1               5                   10
```

(2) INFORMATION FOR SEQ ID NO: 23:

(i) SEQUENCE CHARACTERISTICS:
(A) LENGTH: 19 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 23:

```
Met Asp Phe Gly Leu Ser Leu Val Phe Leu Val Leu Ile Leu Lys Gly
```

-continued

```
1               5                   10                  15

Val Gln Cys


(2) INFORMATION FOR SEQ ID NO: 24:

     (i) SEQUENCE CHARACTERISTICS:
          (A) LENGTH: 30 amino acids
          (B) TYPE: amino acid
          (C) STRANDEDNESS: <Unknown>
          (D) TOPOLOGY: linear

    (ii) MOLECULE TYPE: peptide

    (xi) SEQUENCE DESCRIPTION: SEQ ID NO: 24:

Glu Val Gln Met Val Glu Ser Gly Gly Gly Leu Val Lys Pro Gly Gly
1               5                   10                  15

Ser Leu Lys Leu Ser Cys Ala Ala Ser Gly Phe Ala Phe Ser
            20                  25                  30


(2) INFORMATION FOR SEQ ID NO: 25:

     (i) SEQUENCE CHARACTERISTICS:
          (A) LENGTH: 5 amino acids
          (B) TYPE: amino acid
          (C) STRANDEDNESS: <Unknown>
          (D) TOPOLOGY: linear

    (ii) MOLECULE TYPE: peptide

    (xi) SEQUENCE DESCRIPTION: SEQ ID NO: 25:

Ser Tyr Ala Met Ser
1               5


(2) INFORMATION FOR SEQ ID NO: 26:

     (i) SEQUENCE CHARACTERISTICS:
          (A) LENGTH: 14 amino acids
          (B) TYPE: amino acid
          (C) STRANDEDNESS: <Unknown>
          (D) TOPOLOGY: linear

    (ii) MOLECULE TYPE: peptide

    (xi) SEQUENCE DESCRIPTION: SEQ ID NO: 26:

Trp Val Arg Gln Ser Pro Glu Lys Arg Leu Glu Trp Val Ala
1               5                   10


(2) INFORMATION FOR SEQ ID NO: 27:

     (i) SEQUENCE CHARACTERISTICS:
          (A) LENGTH: 17 amino acids
          (B) TYPE: amino acid
          (C) STRANDEDNESS: <Unknown>
          (D) TOPOLOGY: linear

    (ii) MOLECULE TYPE: peptide

    (xi) SEQUENCE DESCRIPTION: SEQ ID NO: 27:

Glu Ile Ser Ser Gly Gly Asn Tyr Ala Tyr Tyr Gln Asp Thr Val Thr
1               5                   10                  15

Gly


(2) INFORMATION FOR SEQ ID NO: 28:

     (i) SEQUENCE CHARACTERISTICS:
          (A) LENGTH: 32 amino acids
          (B) TYPE: amino acid
```

(C) STRANDEDNESS: <Unknown>
(D) TOPOLOGY: linear (ii) MOLECULE TYPE: peptide (xi) SEQUENCE DESCRIPTION: SEQ ID NO: 28:

```
Arg Phe Thr Ile Ser Arg Asp Asn Ala Lys Asn Thr Leu Tyr Leu Glu
1               5                   10                  15

Met Ser Ser Leu Arg Ser Glu Asp Thr Ala Met Tyr Tyr Cys Ala Arg
            20                  25                  30
```

(2) INFORMATION FOR SEQ ID NO: 29:

(i) SEQUENCE CHARACTERISTICS:
(A) LENGTH: 9 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 29:

```
Glu Gly Ile Pro Ala Trp Phe Ala Tyr
1               5
```

(2) INFORMATION FOR SEQ ID NO: 30:

(i) SEQUENCE CHARACTERISTICS:
(A) LENGTH: 11 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 30:

```
Trp Gly Gln Gly Thr Leu Val Ser Val Ser Ala
1               5                   10
```

(2) INFORMATION FOR SEQ ID NO: 31:

(i) SEQUENCE CHARACTERISTICS:
(A) LENGTH: 21 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 31:

```
Glu Val Gln Met Val Glu Ser Gly Gly Gly Leu Val Lys Pro Gly Gly
1               5                   10                  15

Ser Leu Lys Leu Ser
            20
```

(2) INFORMATION FOR SEQ ID NO: 32:

(i) SEQUENCE CHARACTERISTICS:
(A) LENGTH: 21 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 32:

```
Glu Val Gln Met Val Glu Ser Gly Gly Gly Leu Val Lys Pro Gly Gly
1               5                   10                  15
```

```
Xaa Leu Lys Leu Ser
            20


(2) INFORMATION FOR SEQ ID NO: 33:

     (i) SEQUENCE CHARACTERISTICS:
          (A) LENGTH: 21 amino acids
          (B) TYPE: amino acid
          (C) STRANDEDNESS: <Unknown>
          (D) TOPOLOGY: linear

    (ii) MOLECULE TYPE: peptide

    (xi) SEQUENCE DESCRIPTION: SEQ ID NO: 33:

Asp Val Leu Met Thr Gln Thr Pro Leu Ser Leu Pro Val Ser Leu Gly
1               5                   10                  15

Asp Gln Ala Ser Ile
            20


(2) INFORMATION FOR SEQ ID NO: 34:

     (i) SEQUENCE CHARACTERISTICS:
          (A) LENGTH: 21 amino acids
          (B) TYPE: amino acid
          (C) STRANDEDNESS: <Unknown>
          (D) TOPOLOGY: linear

    (ii) MOLECULE TYPE: peptide

    (xi) SEQUENCE DESCRIPTION: SEQ ID NO: 34:

Asp Val Leu Met Thr Gln Thr Pro Leu Ser Leu Pro Val Xaa Xaa Gly
1               5                   10                  15

Asp Gln Ala Ser Ile
            20


(2) INFORMATION FOR SEQ ID NO: 35:

     (i) SEQUENCE CHARACTERISTICS:
          (A) LENGTH: 21 amino acids
          (B) TYPE: amino acid
          (C) STRANDEDNESS: <Unknown>
          (D) TOPOLOGY: linear

    (ii) MOLECULE TYPE: peptide

    (xi) SEQUENCE DESCRIPTION: SEQ ID NO: 35:

Asp Val Leu Met Thr Gln Thr Pro Leu Ser Leu Pro Val Ser Leu Gly
1               5                   10                  15

Asp Gln Ala Ser Ile
            20


(2) INFORMATION FOR SEQ ID NO: 36:

     (i) SEQUENCE CHARACTERISTICS:
          (A) LENGTH: 21 amino acids
          (B) TYPE: amino acid
          (C) STRANDEDNESS: <Unknown>
          (D) TOPOLOGY: linear

    (ii) MOLECULE TYPE: peptide

    (xi) SEQUENCE DESCRIPTION: SEQ ID NO: 36:

Asp Val Leu Met Thr Gln Thr Pro Leu Ser Leu Pro Val Ser Leu Gly
1               5                   10                  15

Asp Gln Ala Ser Ile
            20
```

(2) INFORMATION FOR SEQ ID NO: 37:

(i) SEQUENCE CHARACTERISTICS:
(A) LENGTH: 50 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 37:

CCCGGATCCT TTAAAAGGTG TCCAGTGTGA AGTGCAGATG GTGGAGTCTG 50

(2) INFORMATION FOR SEQ ID NO: 38:

(i) SEQUENCE CHARACTERISTICS:
(A) LENGTH: 49 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 38:

GAATTCGGGG CTAGCACTAG AGACAGTGAC CAGAGTCCCT TGGCCCCAG 49

(2) INFORMATION FOR SEQ ID NO: 39:

(i) SEQUENCE CHARACTERISTICS:
(A) LENGTH: 101 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 39:

AGTGCAGATG GTGGAGTCTG GGGGAGGCTT AGTGCAGCCT GGAGGGTCCC TGAGACTCTC 60

CTGTGCAGCC TCTGGATTCG CTTTCAGTAG CTATGCCATG T 101

(2) INFORMATION FOR SEQ ID NO: 40:

(i) SEQUENCE CHARACTERISTICS:
(A) LENGTH: 101 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 40:

CTTGATAGTA GGCGTAATTA CCACCACTAC TAATTTCTGC GACCCACTCC AGCCCCTTCC 60

CTGGAGCCTG GCGAACCCAA GACATGGCAT AGCTACTGAA A 101

(2) INFORMATION FOR SEQ ID NO: 41:

(i) SEQUENCE CHARACTERISTICS:
(A) LENGTH: 101 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 41:

TAATTACGCC TACTATCAAG ACACTGTGAC GGGCCGATTC ACCATCTCCA GAGACAATTC 60

-continued

CAAGAACACC CTGTACCTGC AAATGAACAG TCTGAGGGCT G 101

(2) INFORMATION FOR SEQ ID NO: 42:

(i) SEQUENCE CHARACTERISTICS:
(A) LENGTH: 101 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 42:

CCAGAGTCCC TTGGCCCCAG TAAGCAAACC AGGCCGGGAT ACCGTAGTCC TCCCTTGCAC 60

AGTAATACAC GGCCGTGTCC TCAGCCCTCA GACTGTTCAT T 101

(2) INFORMATION FOR SEQ ID NO: 43:

(i) SEQUENCE CHARACTERISTICS:
(A) LENGTH: 66 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 43:

GGGAAGCTTG ATATCCACCA TGAAGTTGCC TGTTAGGCTG TTGGTGCTGA TGTTCTGGAT 60

TCCTGC 66

(2) INFORMATION FOR SEQ ID NO: 44:

(i) SEQUENCE CHARACTERISTICS:
(A) LENGTH: 65 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 44:

AAAGATTCGT CGACTTACGT TTTATTTCCA GCTTGGTCCC CCCTCCGAAC GTGTACGGAA 60

CATGT 65

(2) INFORMATION FOR SEQ ID NO: 45:

(i) SEQUENCE CHARACTERISTICS:
(A) LENGTH: 100 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 45:

CTGATGTTCT GGATTCCTGC TTCCAGCAGT GATGTTTTGA TGACCCAAAC TCCTCTCTCC 60

CTGCCTGTCA CTCCAGGAGA GCCAGCCTCC ATCTCTTGCA 100

(2) INFORMATION FOR SEQ ID NO: 46:

(i) SEQUENCE CHARACTERISTICS:
(A) LENGTH: 100 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 46:

CTGTGGAGAC TGGCCTGGTT TCTGCAGGTA CCATTCTAAA TAGGTGTTTC CATTACTATG 60

TACAATGCTC TGACTAGATC TGCAAGAGAT GGAGGCTGGC 100

(2) INFORMATION FOR SEQ ID NO: 47:

(i) SEQUENCE CHARACTERISTICS:
(A) LENGTH: 100 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 47:

CGAACGTGTA CGGAACATGT GAACCTTGAA AGCAGTAATA AATTCCCACA TCCTCAGCCT 60

CCACTCTGCT GATCTTGAGT GTGAAATCTG TCCCTGATCC 100

(2) INFORMATION FOR SEQ ID NO: 48:

(i) SEQUENCE CHARACTERISTICS:
(A) LENGTH: 394 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 48:

ATGAAGTTGC CTGTTAGGCT GTTGGTGCTG ATGTTCTGGA TTCCTGCTTC CAGCAGTGAT 60

GTTTTGATGA CCCAAACTCC TCTCTCCCTG CCTGTCACTC CAGGAGAGCC AGCCTCCATC 120

TCTTGCAGAT CTAGTCAGAG CATTGTACAT AGTAATGGAA ACACCTATTT AGAATGGTAC 180

CTGCAGAAAC CAGGCCAGTC TCCACAGCTC CTGATCTACA AAGTTTCCAT CCGATTTTCT 240

GGGGTCCCAG ACAGGTTCAG TGGCAGTGGA TCAGGGACAG ATTTCACACT CAAGATCAGC 300

AGAGTGGAGG CTGAGGATGT GGGAATTTAT TACTGCTTTC AAGGTTCACA TGTTCCGTAC 360

ACGTTCGGAG GGGGGACCAA GCTGGAAATA AAAC 394

(2) INFORMATION FOR SEQ ID NO: 49:

(i) SEQUENCE CHARACTERISTICS:
(A) LENGTH: 417 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 49:

ATGGACTTTG GGCTCAGCTT GGTTTTCCTT GTCCTTATTT TAAAAGGTGT CCAGTGTGAA 60

GTGCAGATGG TGGAGTCTGG GGGAGGCTTA GTGCAGCCTG GAGGGTCCCT GAGACTCTCC 120

TGTGCAGCCT CTGGATTCGC TTTCAGTAGC TATGCCATGT CTTGGGTTCG CCAGGCTCCA 180

GGGAAGGGGC TGGAGTGGGT CGCAGAAATT AGTAGTGGTG GTAATTACGC CTACTATCAA 240

GACACTGTGA CGGGCCGATT CACCATCTCC AGAGACAATT CCAAGAACAC CCTGTACCTG 300

CAAATGAACA GTCTGAGGGC TGAGGACACG GCCGTGTATT ACTGTGCAAG GGAGGACTAC 360

GGTATCCCGG CCTGGTTTGC TTACTGGGGC CAAGGGACTC TGGTCACTGT CTCTAGT 417

(2) INFORMATION FOR SEQ ID NO: 50:

(i) SEQUENCE CHARACTERISTICS:
(A) LENGTH: 131 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 50:

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Thr Pro Gly Glu Pro Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Ile Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Ile Tyr Tyr Cys
            100                 105                 110

Phe Gln Gly Ser His Val Pro Tyr Thr Phe Gly Gly Gly Thr Lys Leu
        115                 120                 125

Glu Ile Lys
    130
```

(2) INFORMATION FOR SEQ ID NO: 51:

(i) SEQUENCE CHARACTERISTICS:
(A) LENGTH: 139 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 51:

```
Met Asp Phe Gly Leu Ser Leu Val Phe Leu Val Leu Ile Leu Lys Gly
1               5                   10                  15

Val Gln Cys Glu Val Gln Met Val Glu Ser Gly Gly Gly Leu Val Gln
            20                  25                  30

Pro Gly Gly Ser Leu Arg Leu Ser Cys Ala Ala Ser Gly Phe Ala Phe
        35                  40                  45

Ser Ser Tyr Ala Met Ser Trp Val Arg Gln Ala Pro Gly Lys Gly Leu
    50                  55                  60

Glu Trp Val Ala Glu Ile Ser Ser Gly Gly Asn Tyr Ala Tyr Tyr Gln
65                  70                  75                  80

Asp Thr Val Thr Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110
```

-continued

```
Tyr Tyr Cys Ala Arg Glu Asp Tyr Gly Ile Pro Ala Trp Phe Ala Tyr
        115                 120                 125

Trp Gly Gln Gly Thr Leu Val Thr Val Ser Ser
    130                 135
```

What is claimed as novel in Letters Patent of the United States is:

1. A [modified chimeric] *humanized anti-KC-4* antibody which selectively binds to the human KC-4 antigen, comprising (1) the *humanized* variable regions of the light and heavy chains of an anti-KC-4 murine antibody and (2) light and heavy chain constant regions of a human antibody, wherein the amino acid sequence of the variable regions comprises SEQ ID NOS: 50 and SEQ ID NO: 51.

[2. The antibody of claim 1, wherein 12 amino acids in the light chain framework regions (FRs) are substituted and 7 amino acids in the heavy chain FRs are substituted.]

[3. The antibody of claim 2, wherein said amino acids in said framework regions are amino acids present in equivalent positions in antibodies of species other than murine.]

4. An antibody according to claim 1, further comprising at least one glycosyl residue attached thereto.

5. A composition of matter, comprising the antibody of claim 1 and a carrier.

6. A cancer diagnostic kit, comprising the composition of claim 5, wherein said carrier is a pharmaceutically acceptable carrier for in vivo administration, and wherein said antibody is in radiolabeled form.

7. A cancer therapy kit, comprising the composition of claim 4 in a pharmaceutically-acceptable form, wherein said antibody is in radiolabeled form.

8. An in vitro cancer diagnostic kit, comprising the antibody of claim 1; and a solid support.

9. The in vitro kit of claim 8, further comprising one or more heterologous immunoglobulins that selectively bind to the constant region of the anti-KC-4 antibody.

10. The in vitro kit of claim 9, further comprising a label selected from the group consisting of a radioisotope, an enzyme, a phosphorescent molecule, and a fluorescent molecule, wherein said label is conjugated to said antibody of said immunoglobulin.

11. A [hybridoma] cell expressing the antibody of claim 1.

12. The [hybridoma] cell of claim 11, having the ATCC Accession No. HB 11455 (HuKC4V2).

13. A composition, comprising the [hybridoma] cell of claim 11, and a diluent or a carrier.

*14. A method of determining the presence of cancer cells in a tissue or a blood sample thereof, comprising contacting a tissue or a blood sample with the anti-KC-4 antibody of claim 1 or an antigen binding fragment thereof, and detecting the presence of an immune complex formed between said anti-KC-4 antibody and the KC-4 antigen of said tissue or said blood sample thereof.*

*15. A method according to claim 14, wherein the tissue is excised from a subject prior to being contacted with the anti-KC-4 antibody, and wherein said contacting and detecting steps are carried out in vitro.*

*16. A method according to claim 15, further comprising comparing results obtained by analyzing said formed complexes with a standard cut-off value determined by comparing results obtained for normal and cancer patients' samples wherein a result above a cut-off value is indicative of cancer.*

*17. A method of imaging a cancer, comprising administering a pharmaceutically-acceptable composition comprising an effective imaging amount of the anti-KC-4 antibody of claim 1 or an antigen binding fragment thereof, in radiolabeled form, to a subject suspected of having a primary or metastasized cancer; and detecting any binding of the labeled antibody to cancer cells in the subject by external imaging.*

*18. A method of treating cancer in a subject, comprising administering to a subject in need of treatment an effective therapeutic amount of the antibody of claim 1, wherein the antibody is conjugated to a therapeutic agent.*

*19. A method of purging cancer cells from a biological sample, comprising contacting a biological sample obtained from a subject suspected of having cancer with the antibody of claim 1 and allowing said antibody to bind the KC-4 antigen associated with cancer cells in the sample to form an immune complex between said antibody and the antigen of said biological sample; and removing said immune complex from the biological sample.*

*20. A method according to claim 14, wherein said tissue sample is prepared for immunohistochemical analysis.*

*21. A method of purging cancer cells from a biological sample and replenishing the purged sample to a subject, comprising the method of claim 19, wherein said method further comprises reintroducing the purged biological sample to the subject.*

* * * * *